US009274046B2

(12) United States Patent
Stewart et al.

(10) Patent No.: US 9,274,046 B2
(45) Date of Patent: Mar. 1, 2016

(54) SYSTEM AND METHOD FOR GROSS ANATOMIC PATHOLOGY USING HYPERSPECTRAL IMAGING

(71) Applicant: ChemImage Corporation, Pittsburgh, PA (US)

(72) Inventors: Shona Stewart, Pittsburgh, PA (US); Patrick Treado, Pittsburgh, PA (US); Heather Kirschner, Moon Township, PA (US); Alan Wilson, Moon Township, PA (US); Ryan Priore, Wexford, PA (US); Jeffrey Cohen, Pittsburgh, PA (US); Serena Augustine, Pittsburgh, PA (US)

(73) Assignee: ChemImage Corporation, Pittsburgh, PA (US)

(*) Notice: Subject to any disclaimer, the term of this patent is extended or adjusted under 35 U.S.C. 154(b) by 0 days.

(21) Appl. No.: 13/998,776

(22) Filed: Dec. 3, 2013

(65) Prior Publication Data
US 2014/0093147 A1 Apr. 3, 2014

Related U.S. Application Data

(63) Continuation-in-part of application No. 13/651,600, filed on Oct. 15, 2012, now Pat. No. 8,988,680.

(60) Provisional application No. 61/797,293, filed on Dec. 3, 2012.

(51) Int. Cl.
*G01J 3/28* (2006.01)
*G01N 21/25* (2006.01)
(Continued)

(52) U.S. Cl.
CPC .............. *G01N 21/255* (2013.01); *G01J 3/02* (2013.01); *G01J 3/0224* (2013.01); *G01J 3/32* (2013.01);
(Continued)

(58) Field of Classification Search
CPC ............. G01J 3/02; G01J 3/38; G01J 3/18; G01J 3/2803; G01J 3/2823; G01J 3/443
USPC ..................... 356/300–445, 72–73
See application file for complete search history.

(56) References Cited

U.S. PATENT DOCUMENTS 5,441,047 A 8/1995 David
5,615,673 A 4/1997 Berger
(Continued)

FOREIGN PATENT DOCUMENTS

EP 1196081 4/2002
EP 1835845 9/2007
(Continued)

OTHER PUBLICATIONS

Forms PCT/ISA/220, 210, 237 for international application No. PCT/US2008/001988.
(Continued)

*Primary Examiner* — Abdullahi Nur
(74) *Attorney, Agent, or Firm* — Pepper Hamilton LLP

(57) ABSTRACT

A method for analyzing organ samples using hyperspectral imaging comprising illuminating an organ sample to generate interacted photons, collecting the interacted photons and passing the interacted photons through a tunable filter. The filtered interacted photons are detected to generate a hyperspectral image. A brightfield image is generated and associated with the hyperspectral image. Spectra from locations of interest are extracted and analyzed to assess a characteristic of the organ sample. A system may comprise an illumination source to illuminate an organ sample and generate interacted photons, a collection optics for collecting the interacted photons and a tunable filter to filter the interacted photons. A detector is configured to detect the filtered photons and generate at least one hyperspectral image. The detector may also be configured to generate at least one brightfield image representative of the organ sample.

45 Claims, 19 Drawing Sheets
(6 of 19 Drawing Sheet(s) Filed in Color)

(51) Int. Cl.

| | | |
|---|---|---|
| *G01J 3/02* | (2006.01) | |
| *G01J 3/32* | (2006.01) | |
| *G01J 3/44* | (2006.01) | |
| *G01N 21/31* | (2006.01) | |
| *G01N 21/35* | (2014.01) | |
| *G02B 21/00* | (2006.01) | |
| *G02B 21/16* | (2006.01) | |
| *G02B 21/36* | (2006.01) | |
| *G01N 21/21* | (2006.01) | |
| *G01N 21/33* | (2006.01) | |
| *G01N 21/3581* | (2014.01) | |
| *G01N 21/359* | (2014.01) | |
| *G01N 21/65* | (2006.01) | |

(52) U.S. Cl.
CPC ............... *G01J 3/44* (2013.01); *G01N 21/314* (2013.01); *G01N 21/35* (2013.01); *G02B 21/0092* (2013.01); *G02B 21/16* (2013.01); *G02B 21/361* (2013.01); *G01N 21/21* (2013.01); *G01N 21/33* (2013.01); *G01N 21/359* (2013.01); *G01N 21/3581* (2013.01); *G01N 21/65* (2013.01)

(56) References Cited

U.S. PATENT DOCUMENTS

| | | | |
|---|---|---|---|
| 6,002,476 A | 12/1999 | Treado | |
| 6,018,713 A | 1/2000 | Coll | |
| 6,162,604 A | 12/2000 | Jacob | |
| 6,175,750 B1* | 1/2001 | Cook et al. | 600/310 |
| 6,421,553 B1 | 7/2002 | Costa | |
| 6,620,621 B1 | 9/2003 | Cohenford | |
| 6,640,130 B1 | 10/2003 | Freeman | |
| 6,640,132 B1 | 10/2003 | Freeman | |
| 6,741,884 B1 | 5/2004 | Freeman | |
| 6,751,576 B2 | 6/2004 | Hall | |
| 6,765,668 B2 | 7/2004 | Gardner | |
| 6,810,279 B2 | 10/2004 | Mansfield | |
| 6,864,093 B1 | 3/2005 | Chai | |
| 6,937,885 B1 | 8/2005 | Lewis | |
| 6,949,342 B2 | 9/2005 | Golub | |
| 7,013,172 B2 | 3/2006 | Mansfeld | |
| 7,330,747 B2 | 2/2008 | Maier | |
| 7,394,546 B2 | 7/2008 | Vakhtin | |
| 7,570,356 B2 | 8/2009 | Panza | |
| 7,596,404 B2 | 9/2009 | Maier | |
| 7,692,776 B2 | 4/2010 | Treado | |
| 7,697,576 B2 | 4/2010 | Maier | |
| 7,755,757 B2 | 7/2010 | Maier | |
| 7,808,633 B2 | 10/2010 | Maier | |
| 7,956,996 B2 | 6/2011 | Maier | |
| 7,990,533 B2 | 8/2011 | Maier | |
| 8,004,662 B2 | 8/2011 | Lewis | |
| 8,013,991 B2 | 9/2011 | Maier | |
| 8,081,310 B2 | 12/2011 | Viellerobe | |
| 8,175,688 B2 | 5/2012 | Lewis | |
| 8,224,425 B2 | 7/2012 | Freeman | |
| 8,320,996 B2 | 11/2012 | Panasyuk | |
| 8,374,682 B2 | 2/2013 | Freeman | |
| 8,463,366 B2 | 6/2013 | Lewis | |
| 8,538,507 B2 | 9/2013 | Freeman | |
| 8,548,570 B2 | 10/2013 | Freeman | |
| 2002/0007256 A1 | 1/2002 | Takiue | |
| 2002/0154300 A1* | 10/2002 | Mansfield et al. | 356/300 |
| 2002/0173723 A1 | 11/2002 | Lewis | |
| 2002/0186875 A1 | 12/2002 | Burmer | |
| 2004/0068193 A1 | 4/2004 | Barnes | |
| 2005/0007584 A1 | 1/2005 | Mansfield | |
| 2005/0250091 A1 | 11/2005 | Maier | |
| 2005/0277816 A1 | 12/2005 | Maier | |
| 2006/0155195 A1 | 7/2006 | Maier | |
| 2006/0221335 A1* | 10/2006 | Bangalore et al. | 356/301 |
| 2006/0241497 A1 | 10/2006 | Lewis | |
| 2006/0247514 A1 | 11/2006 | Panasyuk | |
| 2006/0253261 A1 | 11/2006 | Maier | |
| 2006/0281068 A1 | 12/2006 | Maier | |
| 2007/0016079 A1 | 1/2007 | Freeman | |
| 2007/0024946 A1 | 2/2007 | Panasyuk | |
| 2007/0038042 A1 | 2/2007 | Freeman | |
| 2007/0070343 A1 | 3/2007 | Cohen | |
| 2007/0153268 A1 | 7/2007 | Panza | |
| 2007/0178067 A1 | 8/2007 | Maier | |
| 2007/0182959 A1 | 8/2007 | Maier | |
| 2007/0232930 A1 | 10/2007 | Freeman | |
| 2007/0249913 A1 | 10/2007 | Freeman | |
| 2010/0128269 A1* | 5/2010 | Chinowsky et al. | 356/369 |
| 2012/0089030 A1 | 4/2012 | Guze | |
| 2012/0108903 A1 | 5/2012 | Freeman | |
| 2012/0215112 A1 | 8/2012 | Lewis | |
| 2013/0131517 A1 | 5/2013 | Panasyuk | |
| 2013/0137949 A1 | 5/2013 | Freeman | |
| 2013/0237841 A1 | 9/2013 | Freeman | |
| 2013/0245455 A1 | 9/2013 | Freeman | |

FOREIGN PATENT DOCUMENTS

| | | |
|---|---|---|
| EP | 1931262 | 6/2008 |
| EP | 1196081 | 8/2013 |
| WO | 9922640 | 5/1999 |
| WO | 0011295 | 1/2000 |
| WO | 0013578 | 3/2000 |
| WO | 01/03050 | 1/2001 |
| WO | 0101854 | 1/2001 |
| WO | 02065069 | 8/2002 |
| WO | 2006058306 | 6/2006 |
| WO | 2006086085 | 8/2006 |
| WO | 2006107947 | 10/2006 |
| WO | 2006130728 | 12/2006 |
| WO | 2007022508 | 2/2007 |
| WO | 2007035597 | 3/2007 |

OTHER PUBLICATIONS

International Search Report, PCT/US05/42986, mailed Mar. 12, 2007.

International Search Report, PCT/US06/12461, mailed Sep. 25, 2007.

International Search Report, PCT/US06/032593, mailed Aug. 9, 2007.

International Search Report, PCT/US06/36223, mailed Dec. 4, 2007.

* cited by examiner

300

- 310: Illuminating at least a portion of a biological sample to generate at least one plurality of interacted photons
- 320: Collecting the plurality of interacted photons
- 330: Passing the plurality of interacted photons through a filter
- 340: Detecting the plurality of interacted photons
- 350: Extracting at least one spectrum from at least one location of the hyperspectral data set
- 360: Analyzing the extracted spectrum to assess at least one characteristic of the biological sample

FIG. 3

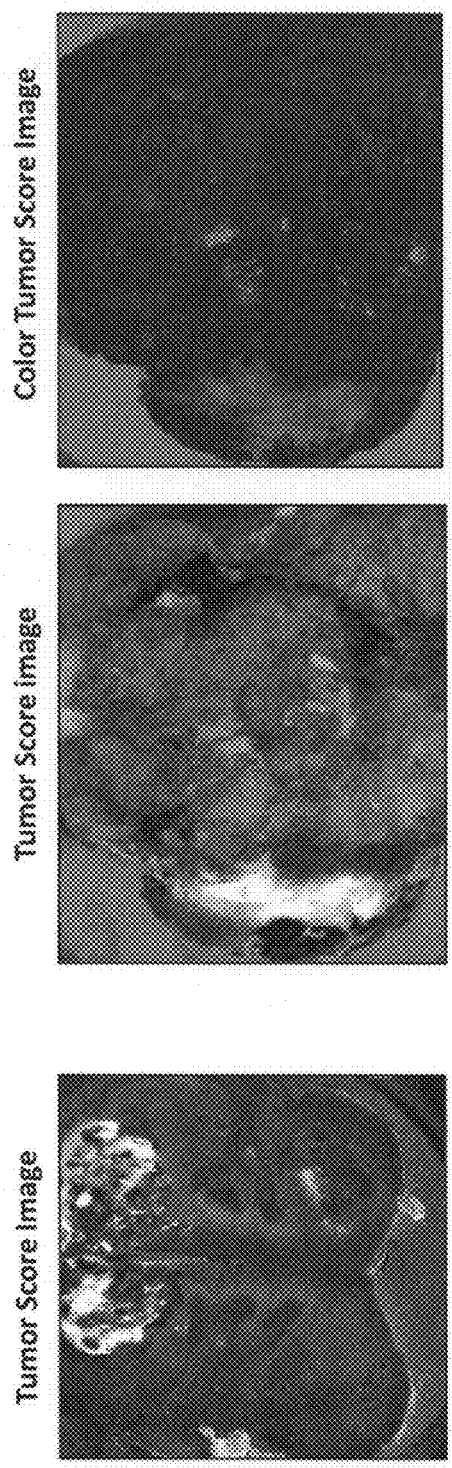

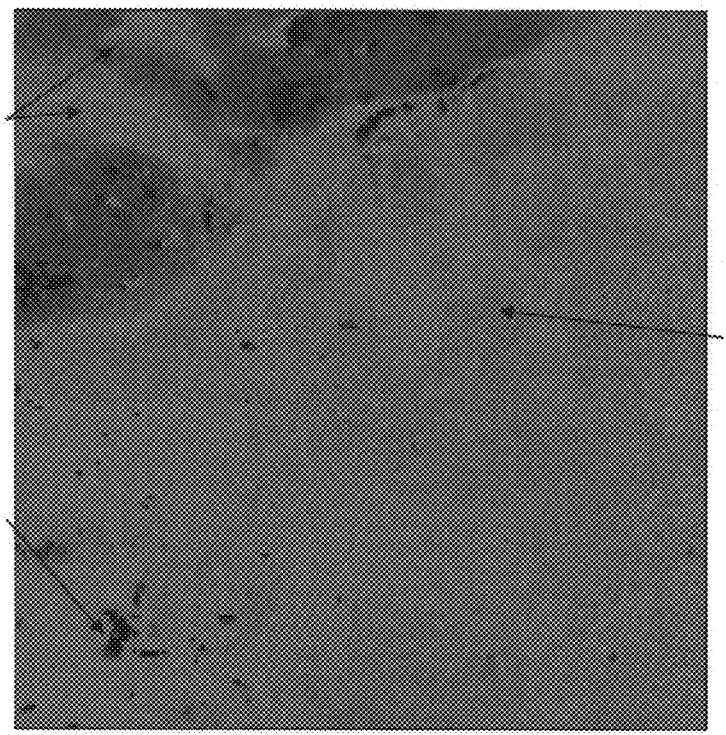
FIG. 13A Brightfield
FIG. 13B Ground Truth
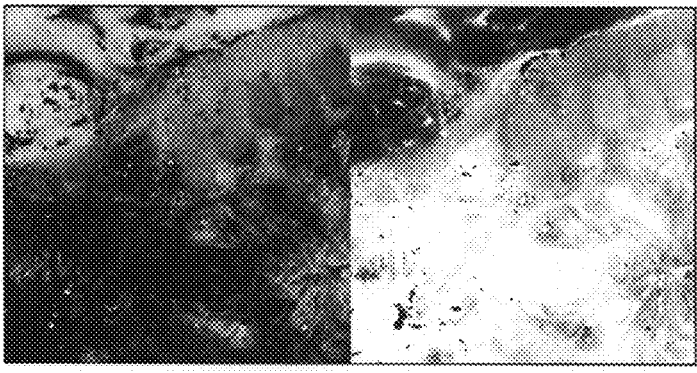
FIG. 13C Fat/NRP Score Image
FIG. 13D Tumor Score Image
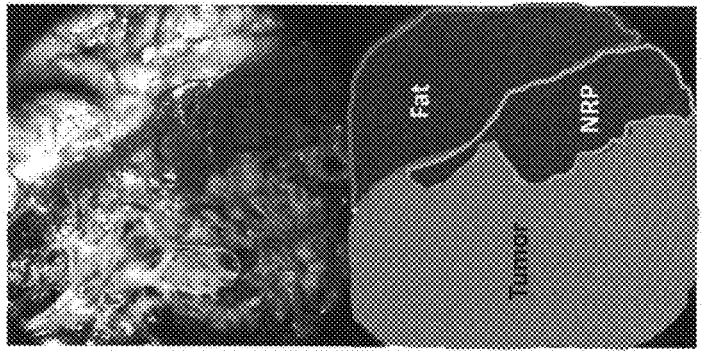
FIG. 13E
Kidney cancer imaging: Digital staining
Representative Kidney, Cropped, Two Class LOPO Model

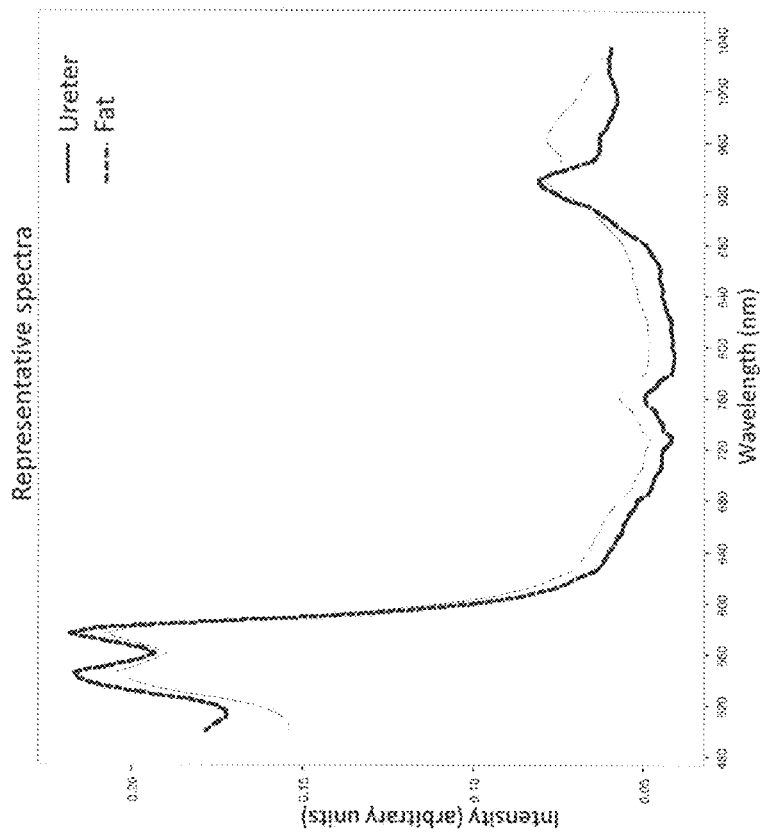
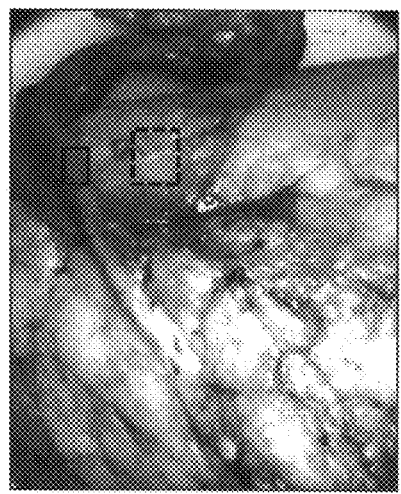
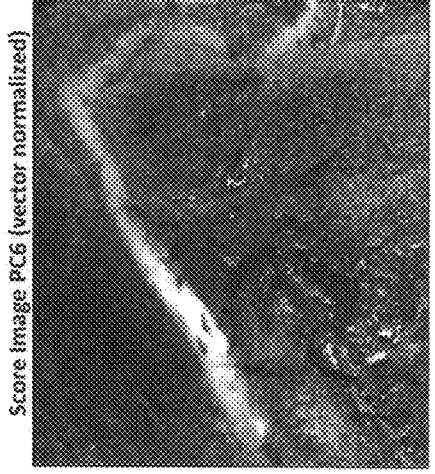
FIG. 16A
FIG. 16B
FIG. 16C

SYSTEM AND METHOD FOR GROSS ANATOMIC PATHOLOGY USING HYPERSPECTRAL IMAGING

RELATED APPLICATIONS

This Application claims priority under 35 U.S.C. §119(e) to pending U.S. Provisional Patent Application No. 61/797,293, filed on Dec. 3, 2012, entitled "Hyperspectral Imaging for Gross Anatomic Pathology." This Application is also a continuation-in-part to pending U.S. patent application Ser. No. 13/651,600, filed on Oct. 15, 2012, entitled "Dual Polarization with Liquid Crystal Tunable Filters." These applications are hereby incorporated by reference in their entireties.

BACKGROUND

Cancer is an enormous global health burden, accounting for one in every eight deaths worldwide. A critical problem in cancer management is the local recurrence of disease, which is often a result of incomplete excision of a tumor. Currently, tissue margins must be identified through histological evaluation of the affected tissue. Approximately one in four patients who undergo tumor resection surgery will require re-operation in order to fully excise the malignant tissue. Recent efforts aimed towards significantly reducing the frequency of location recurrence have employed diffuse reflectance, radiofrequency spectroscopy, and targeted fluorescence imaging. However, there remains an urgent need to develop a highly specific and sensitive system and method for detecting tumor margins that will reduce the risk of cancer recurrence and the need for reoperation.

Current techniques for gross anatomic pathology require inspection by a pathologist and are therefore inherently subjective. There exists a need for a system and method that would enable objective analysis of organs samples. It would be advantageous if the system and method could be used to assess a variety of characteristics of a sample including anatomical features, detecting cancerous tumors, and locating tissue margins.

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors or complementary metal-oxide-semiconductor (CMOS) detectors are typically employed with visible wavelength fluorescence and Raman spectroscopic imaging systems, while indium gallium arsenide (InGaAs) FPA detectors are typically employed with near-infrared spectroscopic imaging systems.

Conventional spectroscopic devices operate over a limited range of wavelengths due to the operation ranges of the detectors, tunable filters, or other possible system components possible. This enables analysis in the UV, VIS, IR, NIR, short wave infrared (SWIR) mid infrared (MIR), and long wave infrared (LWIR) wavelengths and to some overlapping ranges. These correspond to wavelengths of about 180-380 nm (UV), about 380-700 nm (VIS), about 700-2500 nm (NIR), about 850-1700 nm (SWIR), about 2500-5000 nm (MIR), and about 5000-25000 nm (LWIR).

Spectroscopic imaging of a sample can be implemented by one of several methods. First, a point-source illumination can be provided on the sample to measure the spectra at each point of the illuminated area. Line scanning may also be used where data is generated by illuminating a sample with a laser line. Spectra may also be collected over the an entire area encompassing the sample simultaneously using an electronically tunable optical imaging filter such as an acousto-optic tunable filter (AOTF), a multi-conjugate tunable filter (MCF), or a liquid crystal tunable filter (LCTF). Here, the organic material in such optical filters is actively aligned by applied voltages to produce the desired bandpass and transmission function. The spectra obtained for each pixel of such an image thereby forms a complex data set referred to as a hyperspectral image which contains the intensity values at numerous wavelengths or the wavelength dependence of each pixel element in this image. The method selected to generate spectroscopic data may depend on a variety of factors including the nature of the sample being analyzed, time required for analysis, and cost.

A tunable filter uses birefringent retarders to distribute the light energy of an input light signal over a range of polarization states. The polarization state of light emerging at the output of the tunable filter is caused to vary as a function of wavelength due to differential retardation of orthogonal components of the light, contributed by the birefringent retarders. The tunable filter discriminates for wavelength-specific polarization using a polarizing filter at the output. The polarizing filter passes the light components in the output that are rotationally aligned to the polarizing filter. The tunable filter is tuned by adjusting the birefringence of the retarders so that a specific discrimination wavelength emerges in a plane polarized state, aligned to the output polarizing filter. Other wavelengths that emerge in other polarization states and/or alignments are attenuated.

A highly discriminating spectral filter is possible using a sequence of several birefringent retarders. The thicknesses, birefringences, and relative rotation angles of the retarders are chosen to correspond to the discrimination wavelength. More specifically, the input light signal to the filter becomes separated into orthogonal vector components, parallel to the respective ordinary and extraordinary axes of each birefringent retarder when encountered along the light transmission path through the filter. These separated vector components are differentially retarded due to the birefringence; such differential retardation also amounts to a change in their polarization state. For a plane polarized component at the input to the filter, having a specific rotational alignment at the input to the filter and at specific discrimination wavelengths, the light components that have been divided and subdivided all emerge from the filter in the same polarization state and alignment, namely plane polarized and in alignment with the selection polarizer (i.e., the polarizing filter) at the output.

A filter as described is sometimes termed an interference filter because the components that have been divided and subdivided from the input and interfere positively at the output selection polarizer are the components that are passed. Such filters also are sometimes described with respect to a rotational twist in the plane polarization alignment of the discriminated component between the input and the selection polarizer at the output.

There are several known configurations of spectral filters comprising birefringent retarders, such as the Lyot, Solc and Evans types. Such filters can be constructed with fixed (non-tunable) birefringent crystals for the retarders. A filter with retarders that are tuned in unison permits adjustment of the bandpass wavelength. Tunable retarders can comprise liquid crystals or composite retarder elements each comprising a fixed crystal and an optically aligned liquid crystal.

The thicknesses, birefringences, and rotation angles of the retarders are coordinated such that each retarder contributes part of the necessary change in polarization state to alter the polarization state of the passband wavelength from an input reference angle to an output reference angle. The input reference angle may be, for example, 45° to the ordinary and extraordinary axes of a first retarder in the filter. The output reference angle is the rotational alignment of the polarizing filter (or "selection polarizer").

A spectral filter may have a comb-shaped transmission characteristic. Increasing or decreasing the birefringence when tuning to select the discrimination wavelength (or passband), stretches or compresses the comb shape of the transmission characteristic along the wavelength coordinate axis.

If the input light is randomly polarized, the portion that is spectrally filtered is limited to the vector components of the input wavelengths that are parallel to one of the two orthogonal polarization components that are present. Only light at the specific wavelength, and at a given reference polarization alignment at the input, can emerge with a polarization angle aligned to the rotational alignment of the selection polarizer at the output. The light energy that is orthogonal to the reference alignment at the input, including light at the passband wavelength, is substantially blocked.

A tunable filter thus passes only one of two orthogonal components of input light. The transmission ratio in the passband is at a maximum for incident light at the input to the tunable filter that is aligned to a reference angle of the tunable filter. Transmission is at minimum for incident light energy at the input is orthogonal to that reference angle. If the input light in the passband is randomly polarized, the best possible transmission ratio in the passband is fifty percent. It is therefore desirable to devise a system and method wherein both orthogonal components of the input light are allowed to transmit through the tunable filter, thereby effectively doubling the throughput at the filter output.

SUMMARY

The present disclosure provides for a system for analyzing biological samples, such as organs, using hyperspectral imaging. A system may comprise at least one illumination source configured to illuminate a biological sample and generate at least one plurality of interacted photons. A collection optic may be configured to collect the plurality of interacted photons and at least one filter may be configured to filter the interacted photons into a plurality of wavelength bands. At least one detector may be configured to detect the filtered photons and generate at least one hyperspectral image representative of the biological sample.

The present disclosure also provides for a method for analyzing biological samples, such as organs, using hyperspectral imaging. A method may comprise illuminating at least a portion of the biological sample to generate at least one plurality of interacted photons. The interacted photons may be collected and passed through at least one filter to filter the interacted photons into a plurality of wavelength bands. The filtered photons may be detected to generate at least one hyperspectral image representative of the biological sample. At least one spectrum may be extracted from at least one location of the hyperspectral image, wherein each location corresponds to an area of interest of the biological sample. The extracted spectra may be analyzed to assess at least one characteristic of the biological sample.

The present disclosure also provides for a non-transitory data storage medium containing program code, which, when executed by a processor, causes the processor to: illuminate at least a portion of a biological sample, collect the plurality of interacted photons, pass the plurality of interacted photons through at least one filter to filter the interacted photons into a plurality of wavelength bands, detect the plurality of interacted photons to generate at least one hyperspectral image representative of the biological sample, extract at least one spectrum from at least one location of the hyperspectral image, wherein each location corresponds to an area of interest of the biological sample, and analyze the extracted spectrum to thereby assess at least one characteristic of the biological sample.

The system and method of the present disclosure overcome the limitations of the prior art by providing an objective analysis of organ samples without the use of dyes or reagents. Embodiments comprising a dual polarization configuration overcome the limitations of the prior art by maximizing the light transmission ratio during spectrally filtered imaging using a tunable filter. In such embodiments, high throughput, simultaneous data acquisition of more than one wavelength is achievable. The system and method described herein may be used to assess a variety of characteristics of biological samples, including the identification of anatomical features, the presence or absence of cancerous tumors, and the location of tissue margins.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure. The patent or application file contains at least one drawing executed in color. Copies of this patent or patent application publication with color drawing(s) will be provided by the Office upon request and payment of the necessary fee.

FIG. 3 is illustrative of a method of the present disclosure.

FIG. 9A is illustrative of a dissected kidney sample and FIG. 9B is illustrative of an intact kidney sample.

FIGS. 12A-12C are illustrative of the detection capabilities of the present disclosure. FIG. 12A is illustrative of a tumor score image of the dissected kidney. FIG. 12B is illustrative of a tumor score image for an intact kidney. FIG. 12C is illustrative of a "digitally stained" composite score image which is generated by overlaying the digitally stained score images for tumor (green channel) and fat/NRP (blue channel).

FIGS. 13A-13E are illustrative of the detection capabilities of the present disclosure for distinguishing between tumor, normal renal parenchyma (NRP), and fat of a kidney sample. FIG. 13A is illustrative of a brightfield image of a kidney sample. FIG. 13B is illustrative of annotated truth of the kidney sample. FIG. 13C is illustrative of a fat/NRP score image. FIG. 13D is illustrative of a tumor score image. FIG. 13E is illustrative of the ability of the present disclosure to detect a tumor margin.

FIG. 15A is illustrative of a brightfield image of a kidney sample. FIG. 15B is illustrative of annotated truth of the kidney sample. FIG. 15C is illustrative of a "digitally stained" composite score image which is a generated by overlaying the digitally stained score images for tumor (green channel) and fat (red channel), and NRP (blue channel) and is thereby illustrative of the ability of the present disclosure to distinguish between tumor, fat, and NRP.

FIGS. 16A-16C are illustrative of the detection capabilities of the present disclosure for distinguishing between fat and ureter of a kidney sample. FIG. 16A is illustrative of a brightfield image of a kidney sample. FIG. 16B is illustrative of a score image of the kidney sample. FIG. 16C is illustrative of absorbance spectra extracted from locations corresponding to regions of interest in the kidney sample.

DETAILED DESCRIPTION

Reference will now be made in detail to the preferred embodiments of the present disclosure, examples of which are illustrated in the accompanying drawings. Wherever possible, the same reference numbers will be used throughout the drawings to refer to the same or like parts.

Figure 1A:
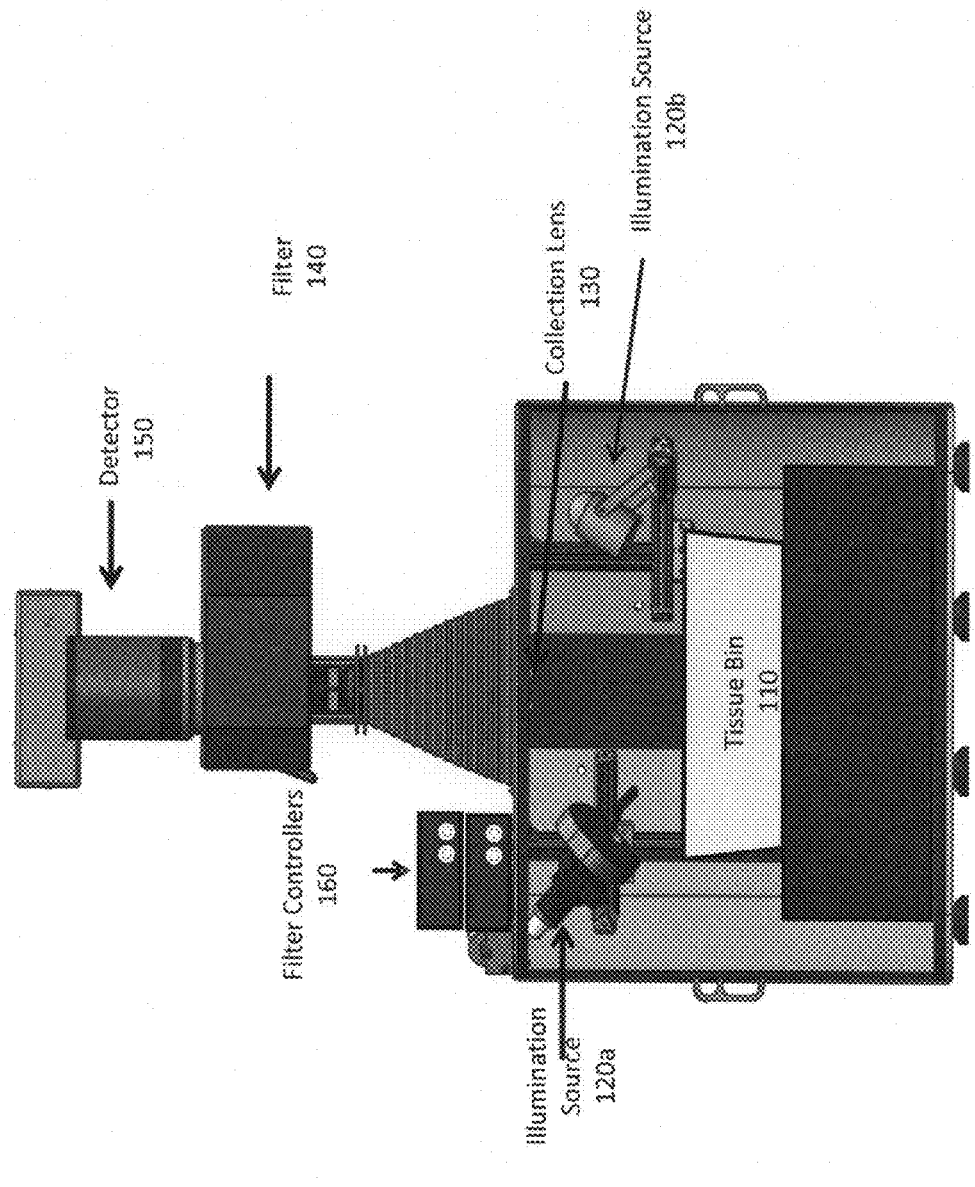
FIG. 1A is illustrative of a system of the present disclosure.
Figure 1B:
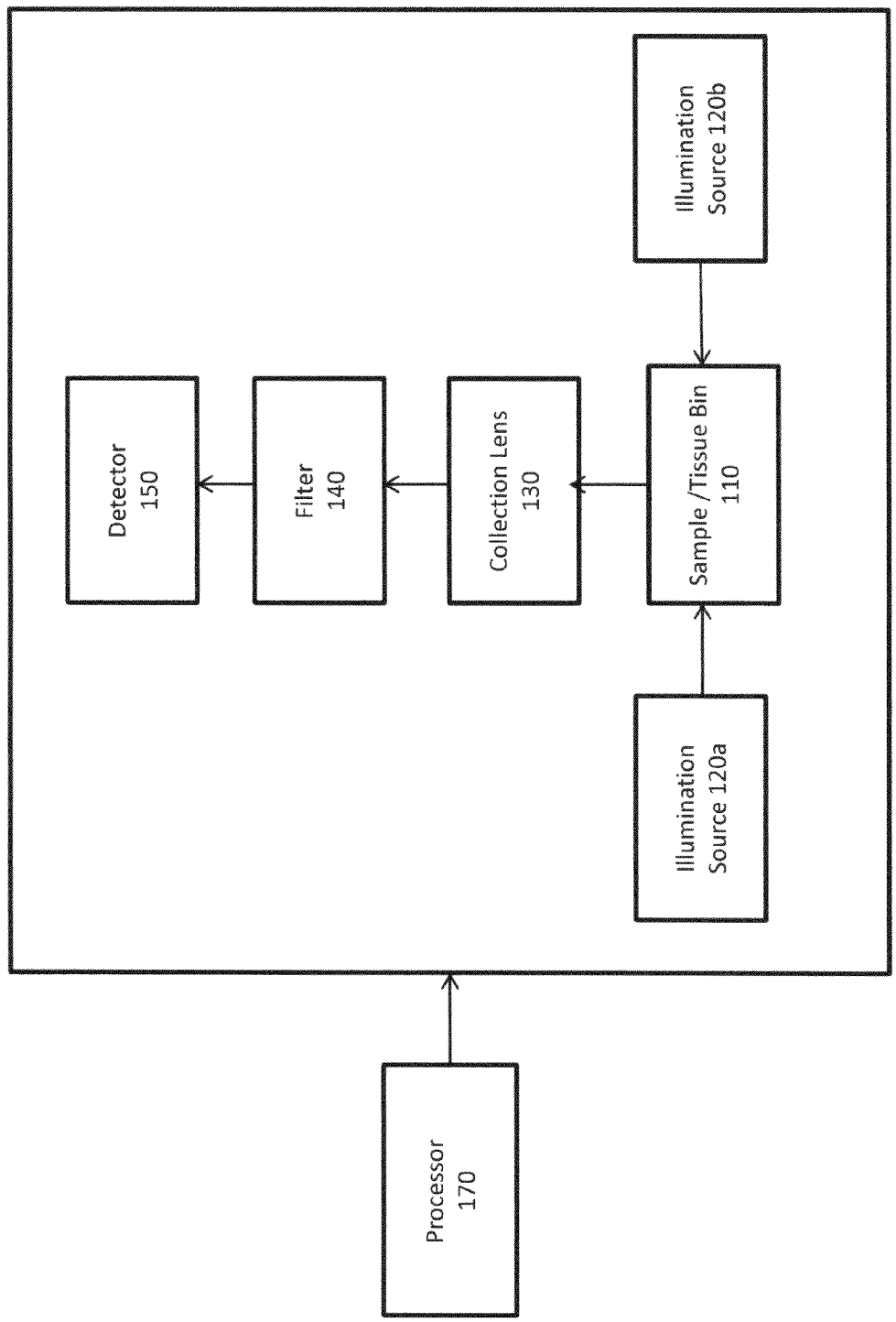
FIG. 1B is illustrative of a system of the present disclosure.

The present disclosure provides for a system for analyzing organ samples using hyperspectral imaging. One embodiment of a system of the present disclosure is illustrated by FIGS. 1A and 1B. The system 100 may comprise a tissue bin 110, or other device, for holding the organ sample under analysis. At least one illumination source may be configured to illuminate a biological sample in tissue bin 110 to generate at least one plurality of interacted photons. In FIGS. 1A and 1B two illumination sources 120a and 120b are illustrated, however, the present disclosure contemplates any number of illumination sources may be used. In one embodiment, at least one illumination source may comprise at least one of: a metal halide arc lamp and a quartz tungsten halogen lamp. Other illumination sources known in the art may also be used.

A collection lens 130 may be configured to collect the plurality of interacted photons. In one embodiment, collection lens 130 may comprise a zoom lens. At least one filter 140 may be configured to filter the interacted photons into a plurality of wavelength bands. In one embodiment, the filter 140 may comprise a fixed filter (such as a thin film fixed bandpass filter). In another embodiment, the filter 140 may comprise a tunable filter. The present disclosure contemplates that either one VIS-NIR tunable filter or a combination of tunable filters (for example, one VIS tunable filter and one NIR tunable filter) may be used to achieve the desired wavelength range. In an embodiment, where two tunable filters are used, software may be configured to automate the acquisition of data in each spectral range and control the movement of system components via a motor. While the embodiments presented herein relate to VIS-NIR hyperspectral imaging, the present disclosure contemplates that other intra and extra corporal imaging techniques known in the art may also be applied.

In one embodiment, the tunable filter further comprises at least one of: a Fabry Perot angle tunable filter, an acousto-optic tunable filter, a liquid crystal tunable filter, a Lyot filter, an Evans split element liquid crystal tunable filter, a Solc liquid crystal tunable filter, a fixed wavelength Fabry Perot tunable filter, an air-tuned Fabry Perot tunable filter, a mechanically-tuned Fabry Perot tunable filter, and a liquid crystal Fabry Perot tunable filter. In one embodiment, one or more controllers 150 may be configured to control the filters to operate over the desired wavelength range.

Referring again to FIG. 1B, a detector 160 may be configured to detect the filtered photons and generate at least one hyperspectral image representative of the biological sample. The detector may comprise at least one of: an indium gallium arsenide (InGaAs) detector, a CMOS detector, a photodiode array, a CCD detector, an intensified charge coupled device (ICCD) detector, a platinum silicide (PtSi) detector, an indium antimonide (InSb) detector, and a mercury cadmium telluride (MCT) detector. In one embodiment, the detector 160 may further be configured to generate a brightfield image of the biological sample.

The system 100 may further comprise at least one processor 170 configured to control various functions of the system 100, store reference data, compare a hyperspectral image with reference data, and/or apply at least one ratiometric or algorithmic technique.

The present disclosure also provides for polarization independent embodiments wherein the transmission ratio is substantially improved by parallel processing of originally orthogonal polarization components through a plurality of spectral filters. Such embodiments may be referred to herein as "dual polarization."

Light is transmitted through a tunable filter, provided that the light is at one of the required discrimination wavelengths defined by the filter transmission characteristic (e.g., a comb filter) and has a predetermined polarization alignment relative to the filter. An input polarization beam splitter might be placed immediately preceding the filter such that only plane polarized light aligned to the necessary reference input polarization angle is admitted to the filter. However, such an input polarization beam splitter is optional because operation of the filter relies on and selects for both the necessary polarization alignment and the necessary wavelength at the input. Thus, the filter can only transmit light that is parallel to the input polarization angle. Therefore, even light that is at the correct wavelength will be blocked by the tunable filter if the polarization alignment of that light at the input to the tunable filter is orthogonal to the predetermined input reference alignment of the tunable filter. This has the adverse effect that if the input polarization orientation is random, then the maximum possible transmission ratio at the discrimination wavelengths is 50%.

Examples of polarization dependent spectral filters include the Lyot, Evans and Sole birefringent filter configurations, originally developed for astrophysical spectral analysis. There are three kinds of basic configurations of stacked polarization interference filters: Lyot filter, Evan split-element filter and Sole filter. The Lyot polarization interference filter was introduced by B. Lyot in 1933 (see, B. Lyot, Comptes Rendues 197, 1593 (1933)). A basic Lyot filter comprises a number of filter stages. Each stage consists of a fixed retarder bounded by linear polarizers. Another stacked polarization interference filter is the Evans split-element filter (see, J. W. Evans, J. Opt. Soc. Am. 39, 229 (1949)), wherein two stages of Lyot filter may be combined into a single stage. In the Evans split-element filter, to eliminate a stage, the birefringent element for the stage to be eliminated is split in half and the split elements are positioned on either side of the birefringent element of another stage. In the Evan filter, the polarizers are crossed, and the center birefringent element is oriented parallel to either polarizer.

Another basic configuration of a stacked polarization interference filter is the Sole filter (see, Sole, J. Opt. Soc. Am. 55, 621 (1965)). Sole filter uses a cascade of identical phase retarders in each stage without the need for polarizers between each of the retarders. Sole filter has two kinds of configurations: Sole fan arrangement and Sole folded arrangement. The first configuration, Sole fan filter, has N identical retarders in each stage—with the rotation angles of $\theta, 3\theta, 5\theta, \ldots (2N-1)\theta$—located between parallel polarizers, where $\theta=\pi/4N$. Another configuration, Sole folded filter, has N identical retarders in each stage with the optical axis of each retarder at $\pm\theta°$ with respect to the entrance polarizer. In the Sole folded filter, the retarders are located between crossed polarizers.

Tunable versions of spectral filters have been developed that include liquid crystal elements capable of being adjusted to determine filter bandpass wavelengths. Tunable filters with cascaded stages are disclosed, for example, in U.S. Pat. Nos. 7,362,489 and 6,992,809—Wang, et al., the disclosure of which are hereby incorporated by reference in their entireties. The U.S. patents discloses embodiments of bandpass filters (MCFs) that may use the Sole filter configurations, e.g., the Sole fan configuration and/or the Sole folded configuration.

The MCF is a type of LCTF which consists of a series of stages composed of polarizers, retarders, and liquid crystals. The MCF is capable of providing diffraction limited spatial resolution, and a spectral resolution consistent with a single stage dispersive monochromator. The MCF may be computer controlled, with no moving parts, and may be tuned to any wavelength in the given filter range. This results in the availability of hundreds of spectral bands. In one embodiment, the individual liquid crystal stages are tuned electronically and the final output is the convolved response of the individual stages. The MCF holds potential for higher optical throughput, superior out-of-band rejection and faster tuning speeds.

LCTFs are designed by using liquid crystal materials as the birefringent elements or using liquid crystal materials as tunable retarders combined with fixed retarders. In the configurations (Lyot, Evan split-element, and Sole) described above, it is observed that LCTFs are sensitive to the polarization state of incident light. LCTFs are inherently sensitive to the polarization state of incident light and capture only one polarization of light, thereby immediately losing one half of the available light.

Figure 2A:
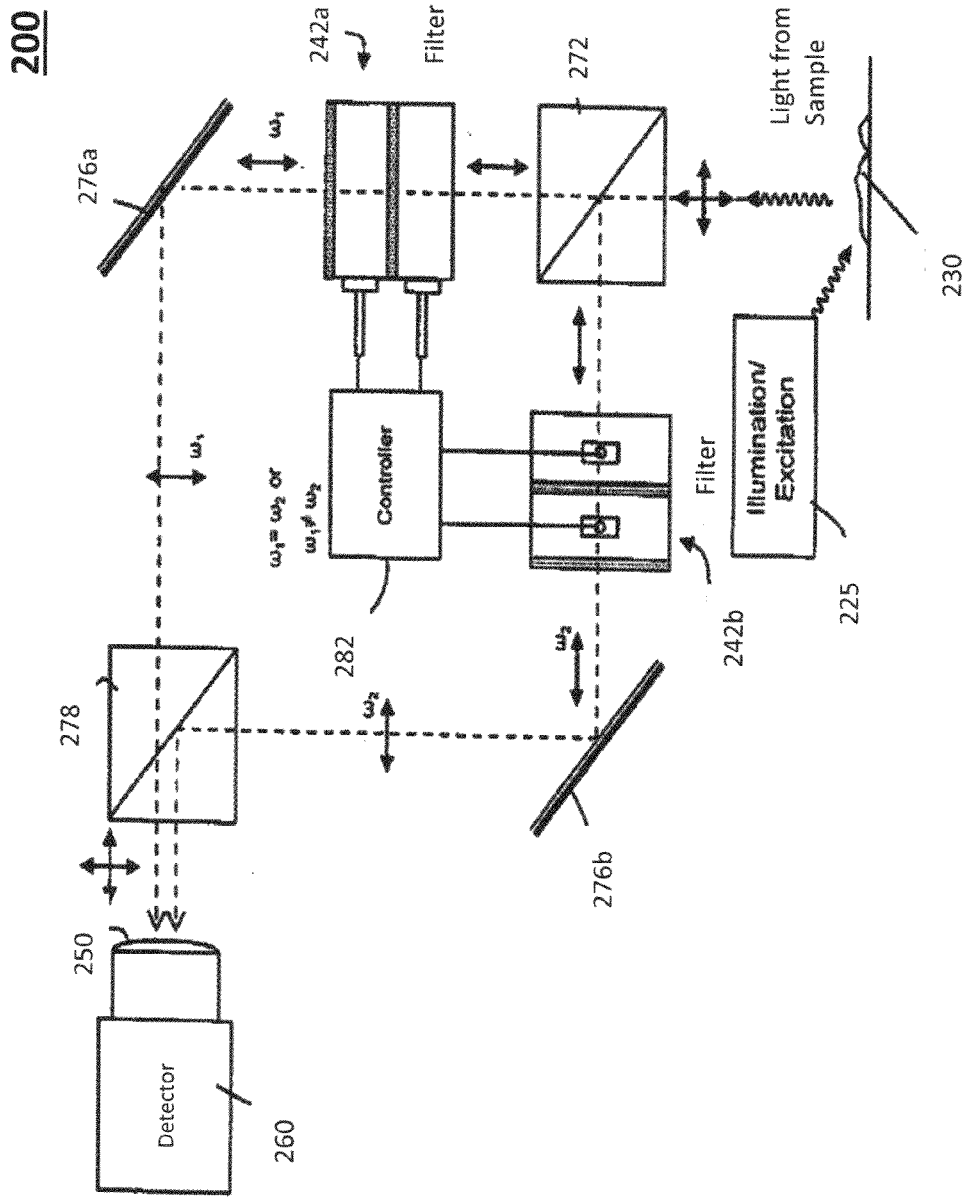
FIG. 2A is illustrative of a dual polarization configuration of a system of the present disclosure.

The embodiment of FIG. 2A comprises two independently tunable filters 242a, 242b along distinct orthogonal beam paths for the orthogonal polarization components emerging from polarizing cube 272. In this arrangement, the paths of the filtered beams are not parallel through the filters 242a, 242b, but are directed by appropriate reflectors (e.g., mirrors) 276a, 276b to a beam combiner 278 (which may be a polarizing cube or polarizing beam splitter as illustrated) at which the orthogonal components, which can be at the same or different passband wavelengths $\omega_1$ and $\omega_2$. In one embodiment, the components may be combined and directed to a detector 260 through a lens assembly 250. In another embodiment, the components may be kept separate as they are directed to the detector 260. However, the beam paths from one beam splitter 272 to the other 278 (via individual filters 242a, 242b) may be made symmetrical to avoid, for example, need for infinitely-corrected optics. In one embodiment, the filters 242a and 242b may comprise at least one of: a fixed filter (such as a thin film fixed bandpass filter) and a tunable filter.

The detector 260 may comprise at least one of: a photodiode array, a CCD detector, an ICCD detector, a CMOS detector, an InGaAs detector, a PtSi detector, InSb detector, MCT detector, and combinations thereof.

In FIG. 2A, in an embodiment where the filters 242a, 242b comprise tunable filters, they may be tuned in unison to the same wavelengths ($\omega_1=\omega_2$) using controller 282. It is possible to configure the controller 282 to independently tune the passband wavelengths $\omega_1$ and $\omega_2$ of the tunable filters 242a, 242b that respectively process orthogonal components of the input. Therefore, by appropriate control, the tunable filters can be tuned to the same wavelength or to two different passband wavelengths ($\omega_1 \neq \omega_2$) at the same time. The controller 282 may be programmable or implemented in software to allow a user to selectively tune each tunable filter 242a, 242b as desired.

Figure 2B:
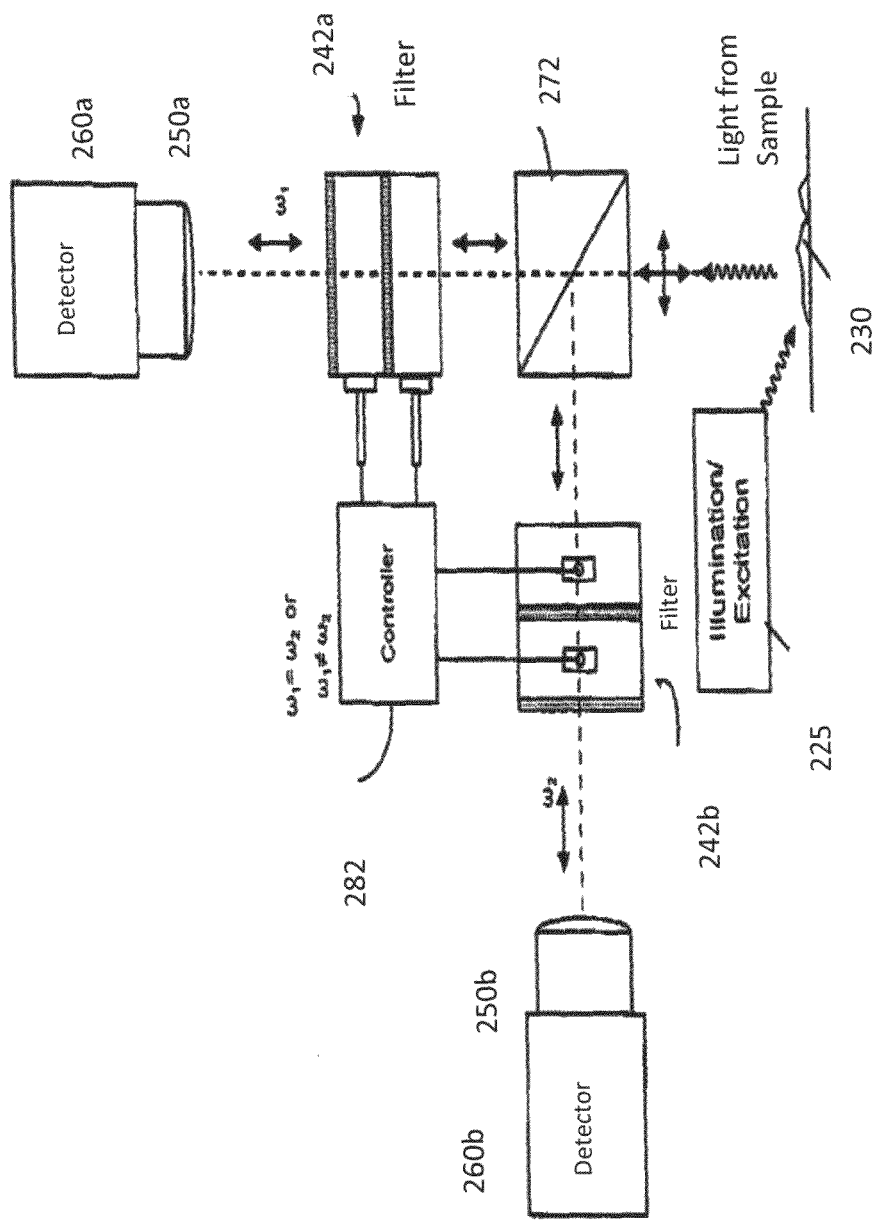
FIG. 2B is illustrative of a dual polarization configuration of a system of the present disclosure.

In the embodiment of FIG. 2A, a fast switching mechanism (not shown) may be provided to switch between the two views (or spectral images) corresponding to spectral data collected by the detector 260 from each of the filters 242a, 242b. Alternatively, two spectral views or images (from two separate filters) may be combined or overlaid into a single image, for example, to increase contrast or intensity or for comparison purposes. The embodiment in FIG. 2A is shown to include a single CCD detector 260 to capture the filtered signals received from the filters 242a, 242b. In another embodiment, the beam combiner 278 may be removed and two detectors may be used. An exemplary embodiment of such a configuration is illustrated in FIG. 2B. Each detector 260a and 260b may be optically coupled to a corresponding one of the two filters 242a, 242b to capture filtered signals from the filter and to responsively generate electronic signals that enable display of spectral images of the illuminated sample 230. The present disclosure contemplates that any number of optical filters and associated detectors may be used to achieve the benefit of dual polarization as described herein.

In one embodiment, the two filtered signals may be detected simultaneously. As discussed herein, simultaneous detection of two different wavelengths holds potential for real-time detection when displayed in a non-overlapping configuration (side-by-side, top to bottom, etc.). In another embodiment, the two filtered signals may be detected sequentially.

It is noted here that although laser light may be coherent, the light received from the sample 230 (e.g., light emitted, scattered, absorbed, and/or reflected) and fed to the filters 242a, 242b may not be coherent. Therefore, wavefront errors may not be present or may be substantially avoided in the two filter versions in FIGS. 2A and 2B because of processing of non-coherent light by each filter 242a, 242b.

The present disclosure also provides for a method for analyzing biological samples, such as organ samples, using hyperspectral imaging. The present disclosure contemplates a variety of organ types may be analyzed using the system and method provided herein, including but not limited to: a kidney, a ureter, a prostate, a penis, a testicle, a bladder, a heart, a brain, a liver, a lung, a colon, an intestine, a pancreas, a thyroid, an adrenal gland, a spleen, a stomach, a uterus, and an ovary.

In one embodiment, illustrated by FIG. 3, the method 300 may comprise illuminating at least a portion of a biological sample in step 310 to generate at least one plurality of interacted photons. These interacted photons may comprise at least one of: photons absorbed by the biological sample, photons reflected by the biological sample, photons scattered by the biological sample, and photons emitted by the biological sample. The interacted photons may be collected in step 320 and passed through at least one filter in step 330 to filter the interacted photons into a plurality of wavelength bands. In one embodiment, step 330 may further comprise passing the interacted photons through at least one of: a fixed filter (such as a thin film fixed bandpass filter) and a tunable filter.

In step 340, the filtered photons may be detected and at least one hyperspectral image may be generated representative of the biological sample. In one embodiment, the hyperspectral image may comprise at least one VIS-NIR hyperspectral image. In one embodiment, each pixel of the image comprises at least one spectrum representative of the biological material at that location in the biological sample. In one embodiment, the method 300 may further comprise the use of dual polarization. In such an embodiment, the interacted photons may be separated into two orthogonally-polarized components (photons corresponding to a first optical component and photons corresponding to a second optical component). The first optical component may be transmitted to a first filter and the second optical component may be transmitted to a second filter. The photons associated with each component may be filtered by the corresponding filter to generate filtered photons.

The filtered photons may be detected to generate at least one hyperspectral image. In one embodiment, filtered photons corresponding to a first optical component may be detected by a first detector and filtered photons corresponding to a second optical component may be detected by a second detector. The present disclosure contemplates the hyperspectral images may be overlaid or displayed in a configuration other than overlaid. The present disclosure also contemplates the filtered photons may be detected either simultaneously or sequentially.

In one embodiment, a brightfield image of the biological sample may be generated. The present disclosure contemplates several methods may be used to generate a brightfield image which would not require further configuration of a detector. In one embodiment, a reflectance hypercube can be generated and contracted. A plurality of frames corresponding to a desired wavelength range may be extracted from the hypercube using ChemImage Xpert® software, available from ChemImage Corporation, Pittsburgh, Pa. In one embodiment, the range may comprise at least one of: approximately 400 nm-710 nm and approximately 380 nm-700 nm. The software may convert the visible hyperspectral image into a brightfield image using the Wavelength Color Transform (WCT) function; this function applies red, green, and blue coloration, proportionate to pixel intensity, to the 610-710 nm, 505-605 nm, and 400-500 nm frames, respectively. The result is an RGB (WCT) image that is derived from the hypercube.

The brightfield image may be further analyzed and/or annotated to assess various features such as morphological features and/or anatomic features. In addition, the present disclosure also contemplates traditional digital images may be obtained of the biological sample for annotation and to aid in analysis. This annotation may be performed by a surgeon, pathologist, or other clinician.

In step 350, at least one spectrum may be extracted from at least one location corresponding to a region of interest of the biological sample. In one embodiment, a plurality of spectra from multiple locations may be extracted, wherein each location corresponds to a region of interest of the biological sample. For example, in one embodiment, a plurality of spectra may be extracted from the hyperspectral image at a location corresponding to a region of the biological sample suspected to be a cancerous tumor and a plurality of spectra may be extracted from a region of the sample corresponding to a region of the biological sample suspected to be non-tumor (normal) tissue. In another embodiment, spectra may be extracted from various locations of an organ to help identify various anatomical features and/or tissue margins.

In step 360, the extracted spectra may be analyzed to assess at least one characteristic of the biological sample. In one embodiment, the present disclosure contemplates analyzing the spectra by applying at least one algorithm. In one embodiment, supervised classification of the data may be achieved by applying a multivariate analytical technique such as support vector machines (SVM) and/or relevance vector machines (RVM).

In another embodiment, the present disclosure contemplates the algorithmic technique may comprise at least one chemometric technique. Examples of chemometric techniques that may be applied include, but are not limited to: multivariate curve resolution, principle component analysis (PCA), partial least squares discriminant analysis (PLSDA), k means clustering, band t. entropy method, adaptive subspace detector, cosine correlation analysis, Euclidian distance analysis, partial least squares regression, spectral mixture resolution, a spectral angle mapper metric, a spectral information divergence metric, a Mahalanobis distance metric, and spectral unmixing.

The present disclosure provides for three different embodiments applying PLSDA. A prediction from PLSDA is usually a value between zero and one, where one indicates membership within a class and zero indicates non-membership within a class.

In a first embodiment, a traditional two-class model may be used to assess two characteristics of the biological sample. Examples of characteristics analyzed using a two-class model may include, but are not limited to: tumor v. non-tumor, cancer v. non-cancer, and specific anatomical features v. features comprising the remainder of the biological sample.

In a two-class model, extracted spectra and/or reference spectra may be selected for each class. The spectra may be pre-processed by applying techniques such as spectral truncation (for example in a range of approximately 560 nm-1035 nm) and vector normalization. A leave one patient out (LOPO) PLSDA analysis may be applied using the constructed spectral models to detect the "target" class (for example, tumor). Here, each time the model is built, all spectra from one patient is left out of the training set of data used to build the model. The data for the patient that is left out is used as the test set.

Partial Least Squares (PLS) factor selection is an important step in PLSDA model building/evaluation process. The retention of too many PLS factors leads to overfitting of the class/spectra data which may include systematic noise sources. The retention of too few PLS factors leads to underfitting of the class/spectra data. A confusion matrix is typically employed as a Figure of Merit (FOM) for the optimal selection of PLS factors. A misclassification rate for the PLSDA model is evaluated as a function of PLS factors retained. The misclassification rate, although an important parameter, is not very descriptive of the final ROC curve which is the basis for model performance. This method uses an alternative FOM for the optimal selection of PLS factors based upon parameters from the ROC curve such as the Area Under the ROC (AUROC) as well as the minimum distance to an ideal sensor. This approach overcomes the limitations of the prior art because ROC curves are not currently used for selecting factors. The ROC curve is traditionally created at the end of an evaluation process to determine the performance of the model, not to select parameters for building the model.

A model may be built using all patients and an optimal number of factors. A ROC curve may be generated and analyzed. A ROC curve is a plot of sensitivity (true positive rate) and 1-specificity (false positive rate) and may be used as a test to select a threshold score that maximizes sensitivity and specificity. The threshold corresponds to the optimal operating point on the ROC curve that is generated by processing the training data. It is selected such that the performance of the classifier is as close to an ideal sensor as possible. An ideal sensor has a sensitivity of 100%, a specificity equal to 100%, an AUROC of 1.0, and is represented by the upper left corner of the ROC plot. To select the optimal operating point, a threshold is swept across the observed indices. The true positive, true negative, false positive, and false negative classifications are calculated at each threshold value to yield the sensitivity and specificity results. The optimal operating point is the point on the ROC curve that is the minimum distance from the ideal sensor. The threshold that corresponds to this sensitivity and specificity is selected as the threshold for the model. Alternatively, the threshold can be calculated by using a cluster method, such as Otsu's method. A histogram may be calculated using the scores from the training data, and Otsu's method splits the histogram into two parts or classes. The result of applying a threshold to an image may be referred to as a class image.

The two class model may be applied to the spectrum at each pixel in the hyperspectral image to generate two score images, one corresponding to a characteristic of interest (a target image) and one corresponding to a non-target image. A score between 0 and 1 is assigned to the spectrum associated with each pixel and represents the probability that the tissue at that location is the target. These probabilities are directly correlated to the intensity of each pixel in a grayscale (e.g. score) image that is generated for each sample. Software, such as ChemImage Xpert®, may be utilized to digitally stain (add coloration) to the score image and create an RGB image (green=tumor, blue=non-tumor).

In one embodiment, the method may further comprise generating a mask image. Here, a region of interest may be selected from the hyperspectral image and a binary image is generated from the region of interest. An intensity of one may be used for the sample and an intensity of zero may be used for pixels that do not correspond to the sample (the background). The tumor and non-tumor score images may be multiplied by the mask to cut out the non-relevant pixels (background). After the non-relevant pixels are cut out, the image may be digitally stained.

The present disclosure provides for several examples of the detection capabilities of the present disclosure using a two-class PLSDA model. Organ samples illustrated in these examples were obtained immediately after surgical excision, preserved in saline and analyzed using the CONDOR™ imaging system available from ChemImage Corporation, Pittsburgh, Pa. Illumination intensity was optimized using a reflectance standard and hyperspectral images were generated using two LCTFs (one for the VIS region and one for the NIR region).

In an alternative embodiment, hyperspectral images may be generated at only two wavelengths of interest as opposed to many images generated over the desired wavelength range. For example, in an embodiment utilizing thin film fixed bandpass filters, a univariate response is generated in which two wavelengths can be measured. A ratiometric image may be generated by applying at least one ratiometric technique (such as wavelength division). Here, spectra are not extracted from the hyperspectral image and analyzed.

Figure 4:
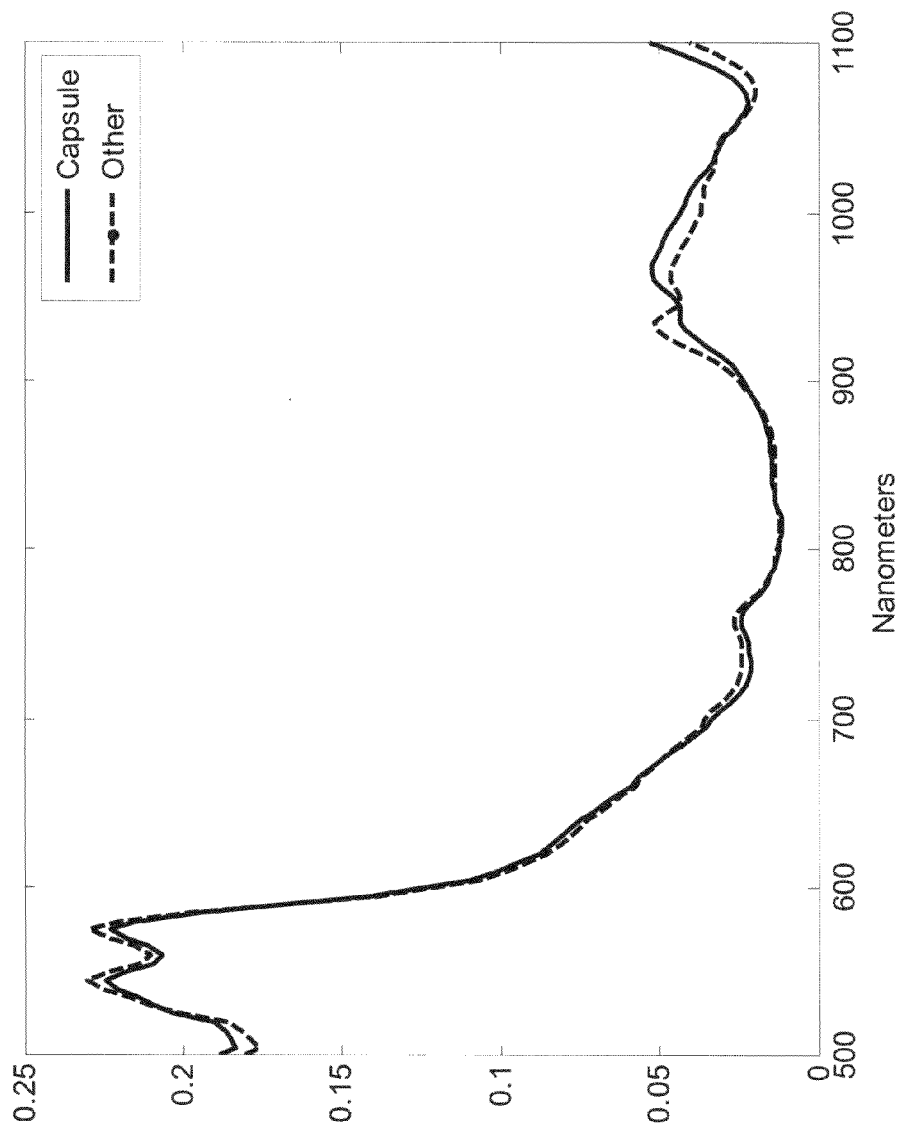
FIG. 4 is illustrative of average prostate absorbance spectra that may be extracted from hyperspectral image data according to the system and method of the present disclosure.
Figure 5:
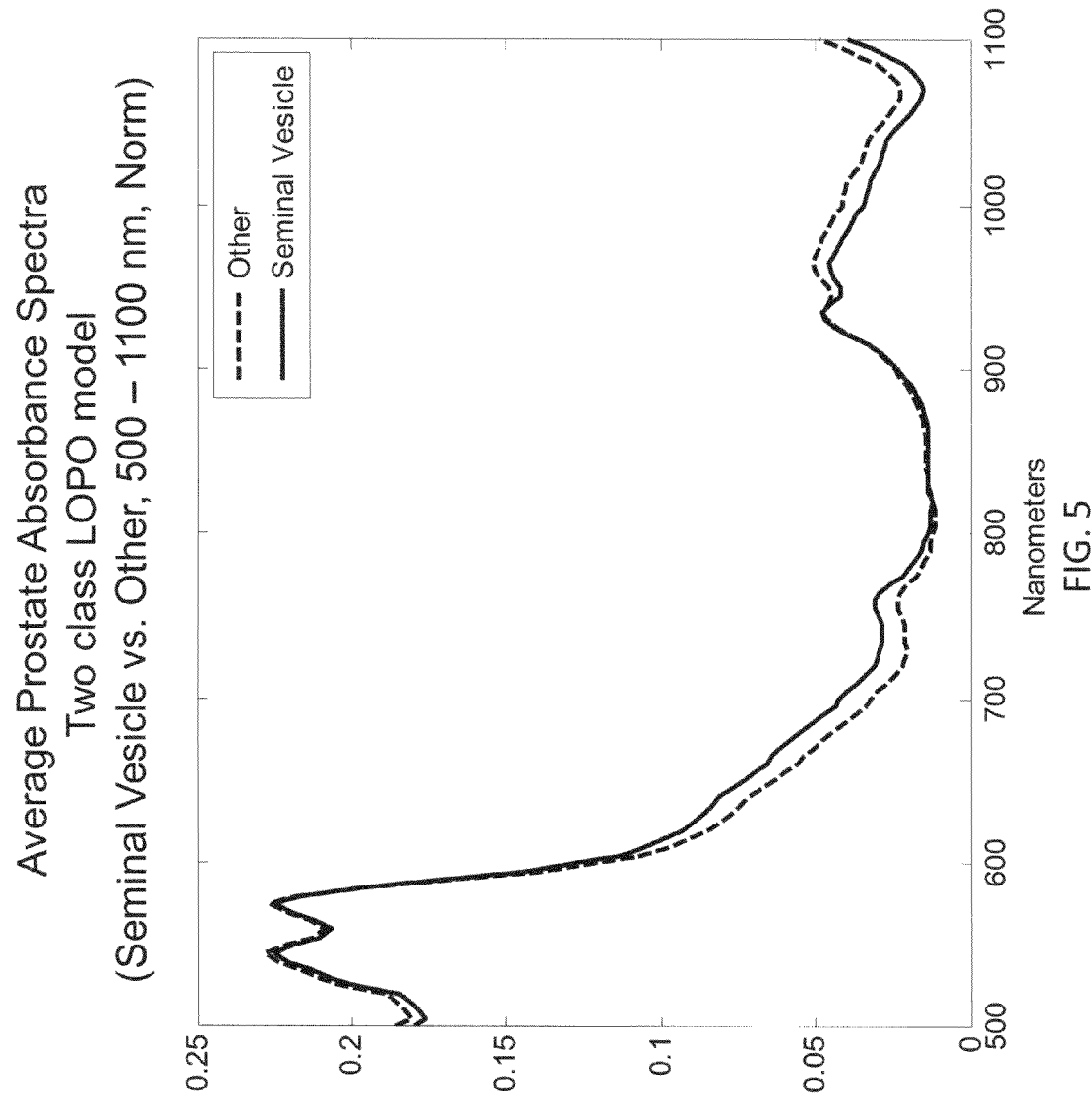
FIG. 5 is illustrative of average prostate absorbance spectra that may be extracted from hyperspectral image data according to the system and method of the present disclosure.
Figure 6:
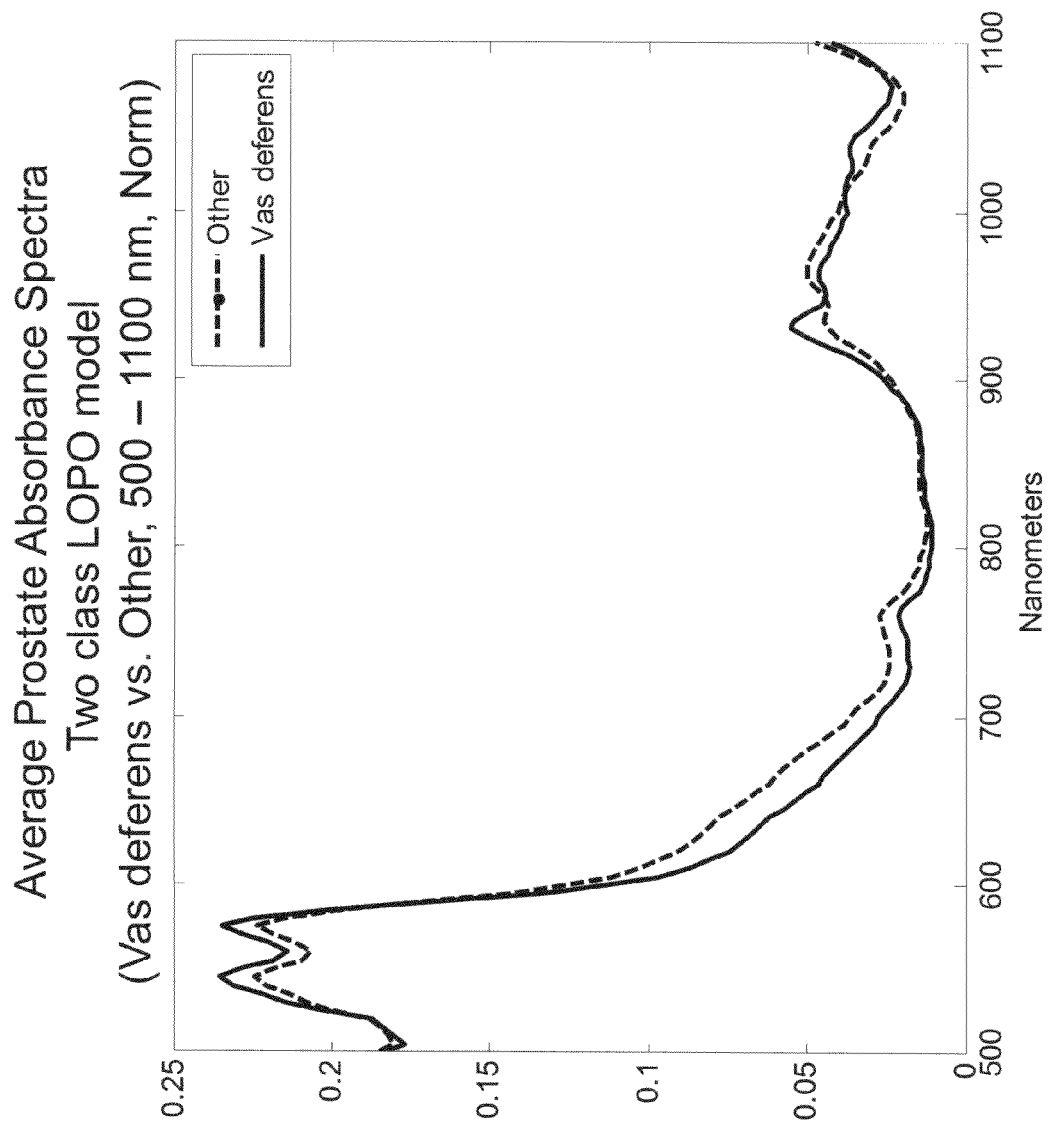
FIG. 6 is illustrative of average prostate absorbance spectra that may be extracted from hyperspectral image data according to the system and method of the present disclosure.

FIGS. 4-6 are illustrative of average spectra corresponding to various characteristics (anatomical features) of a prostate sample collected from a population of samples. FIG. 4 illustrates average spectra of capsule v. other anatomical features of the prostate sample, FIG. 5 illustrates average spectra of seminal vesicle v. other anatomical features of the prostate sample, and FIG. 6 illustrates average spectra of vas deferens v. other anatomical features of the prostate sample.

Figure 7:
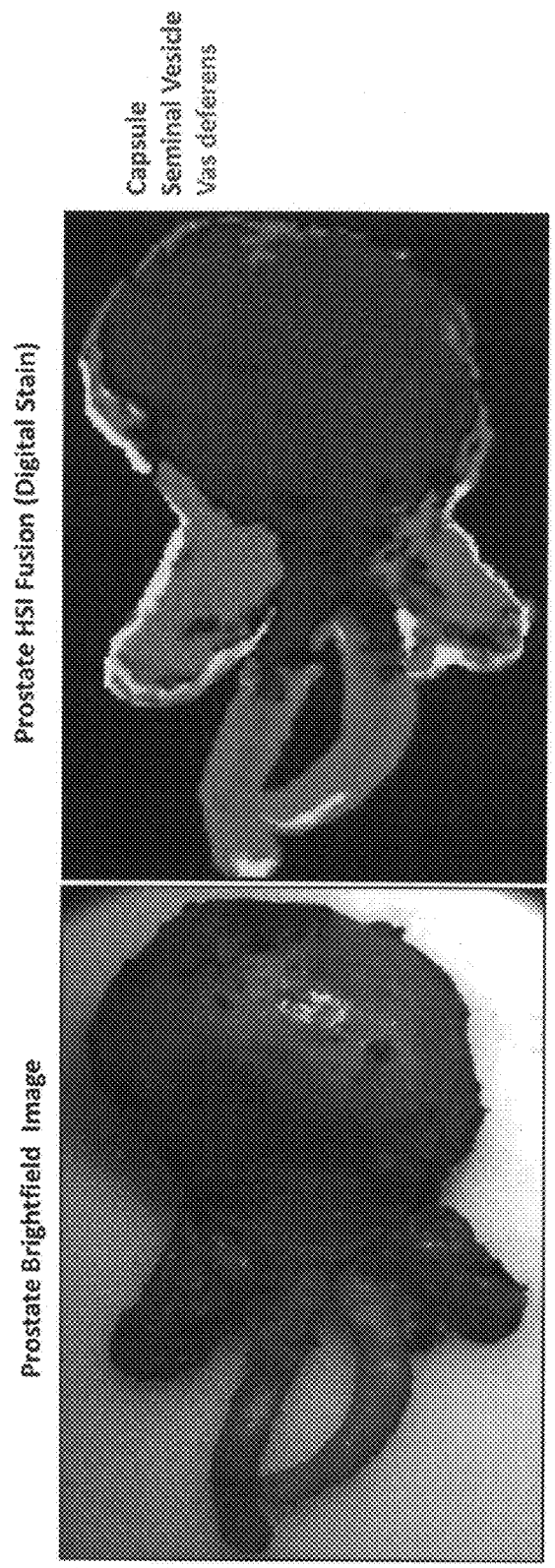
FIG. 7 is illustrative of the detection capabilities of the present disclosure for assessing anatomical features of an organ sample.
Figure 8:
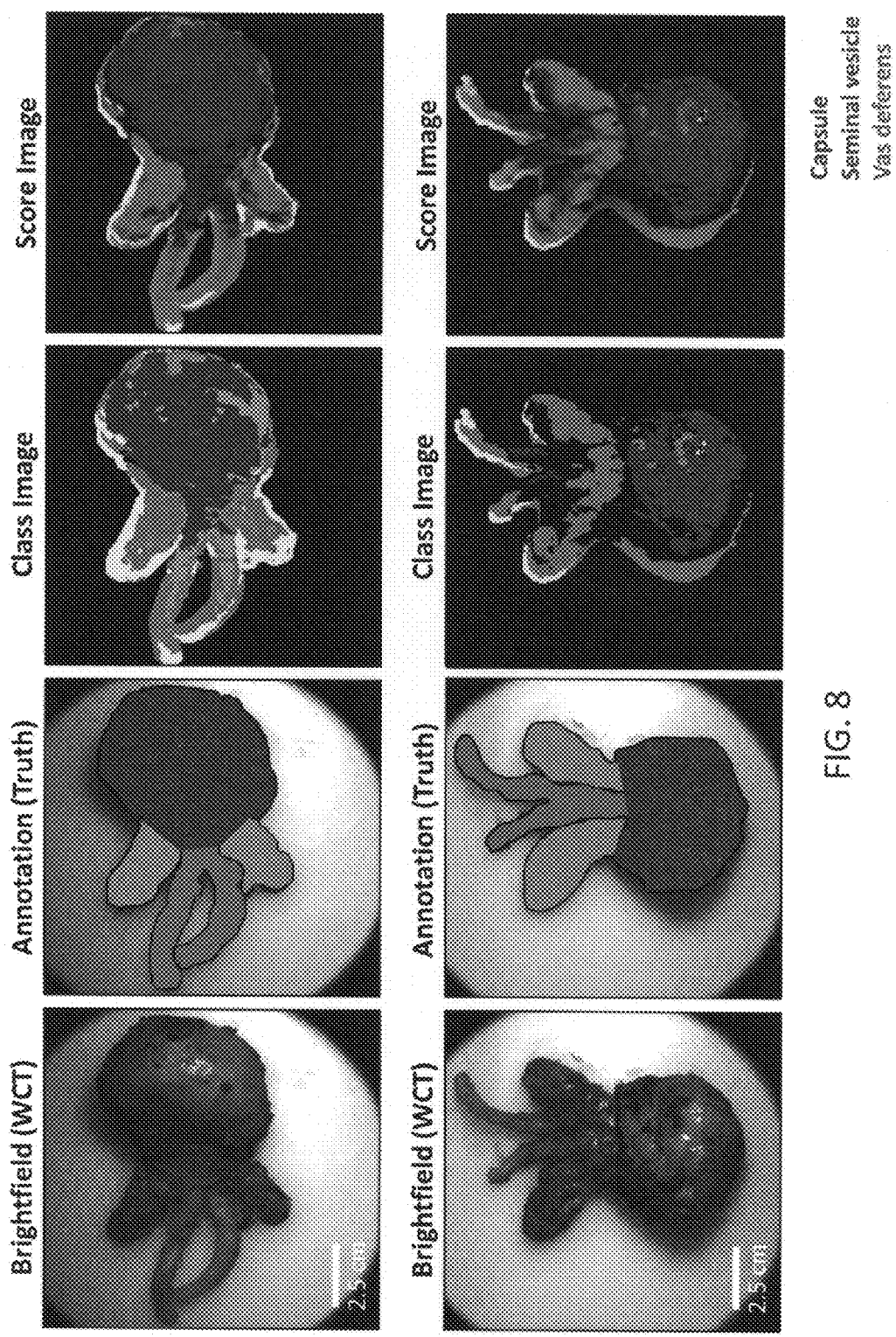
FIG. 8 is illustrative of the detection capabilities of the present disclosure for assessing anatomical features of an organ sample.

The individual spectra from which these average spectra were derived may be used to build the PLSDA model. Test data (spectra extracted from a hyperspectral image of a patient under analysis) may be analyzed by applying the model. Examples of a two-class PLSDA analysis of a prostate sample are illustrated in FIGS. 7-8. In FIG. 7, the prostate image is digitally stained to distinguish between different anatomical features. The capsule, seminal vesicle, and vas deferens are clearly identified.

FIG. 8 illustrates the detection capabilities of the present disclosure as compared to an annotated, or "truth" image. Here, brightfield images were generated for two different views of the prostate sample. A clinician annotated the images to correspond to different anatomical features. A two-class PLSDA model was applied to a hyperspectral image and score images were generated for each anatomical feature. A threshold was applied to generate class images. As can be seen from FIG. 8, various anatomical features were successfully detected.

Figure 9:
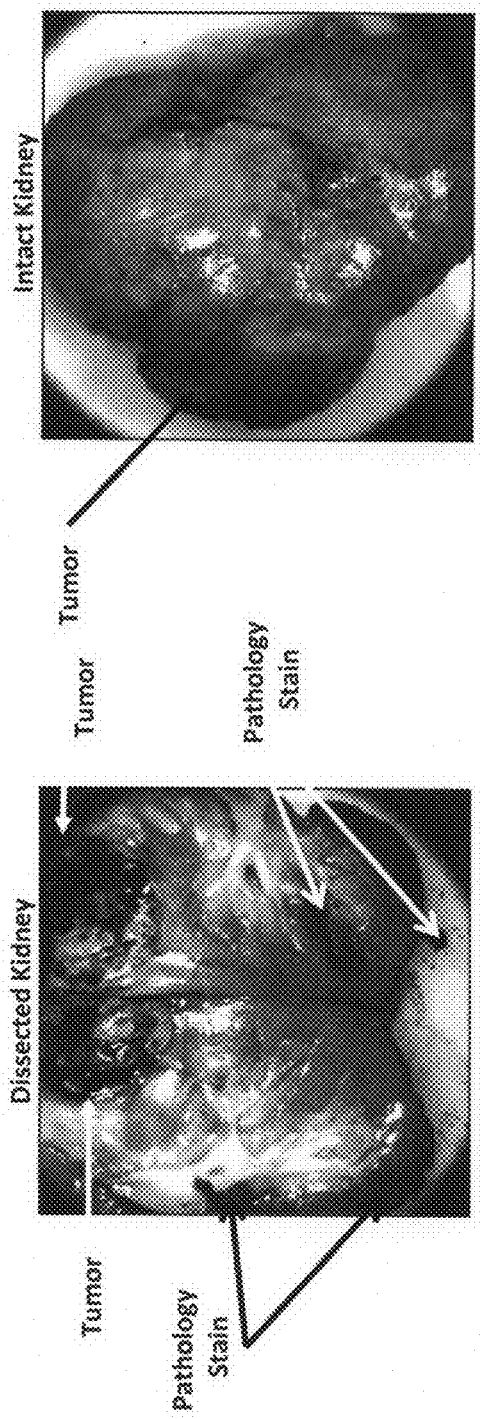
FIGS. 9A-9B are illustrative of digital images of a kidney sample.
Figure 10:
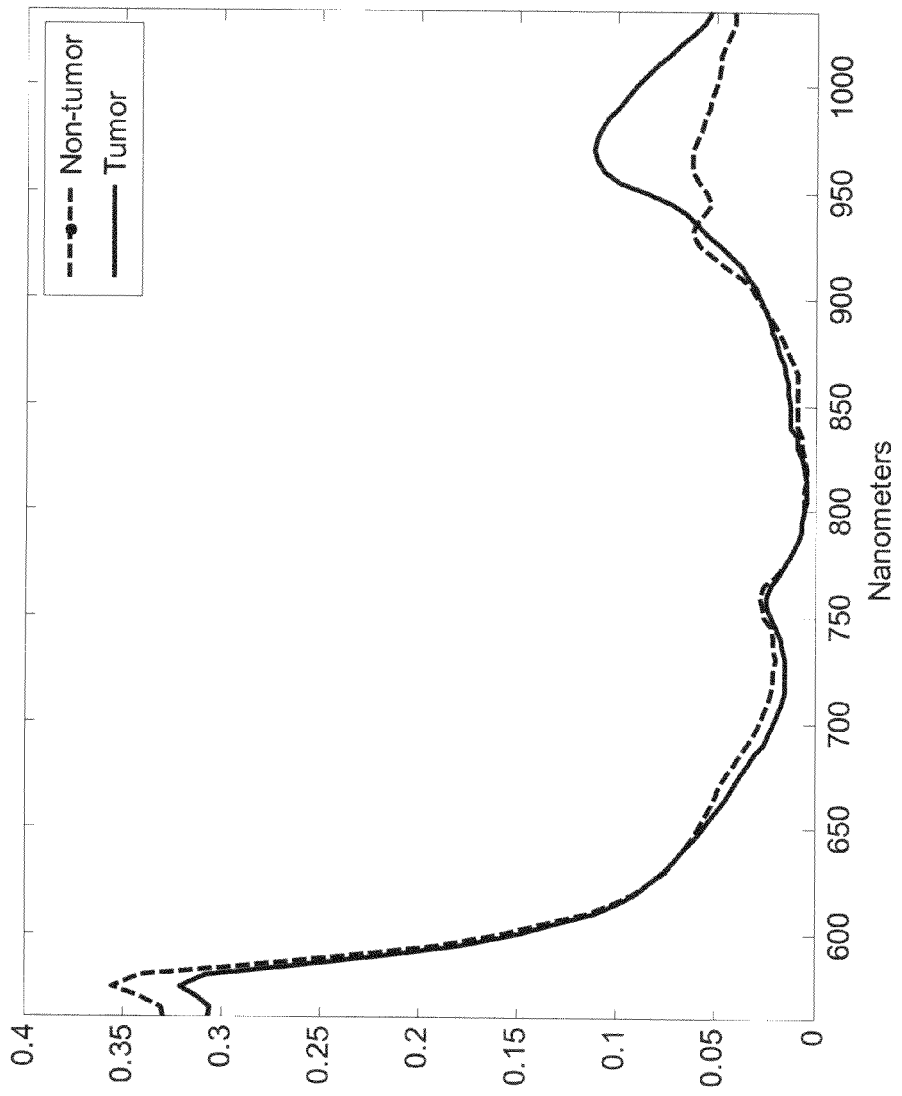
FIG. 10 is illustrative of average kidney absorbance spectra that may be extracted from hyperspectral image data according to the system and method of the present disclosure.
Figure 11:
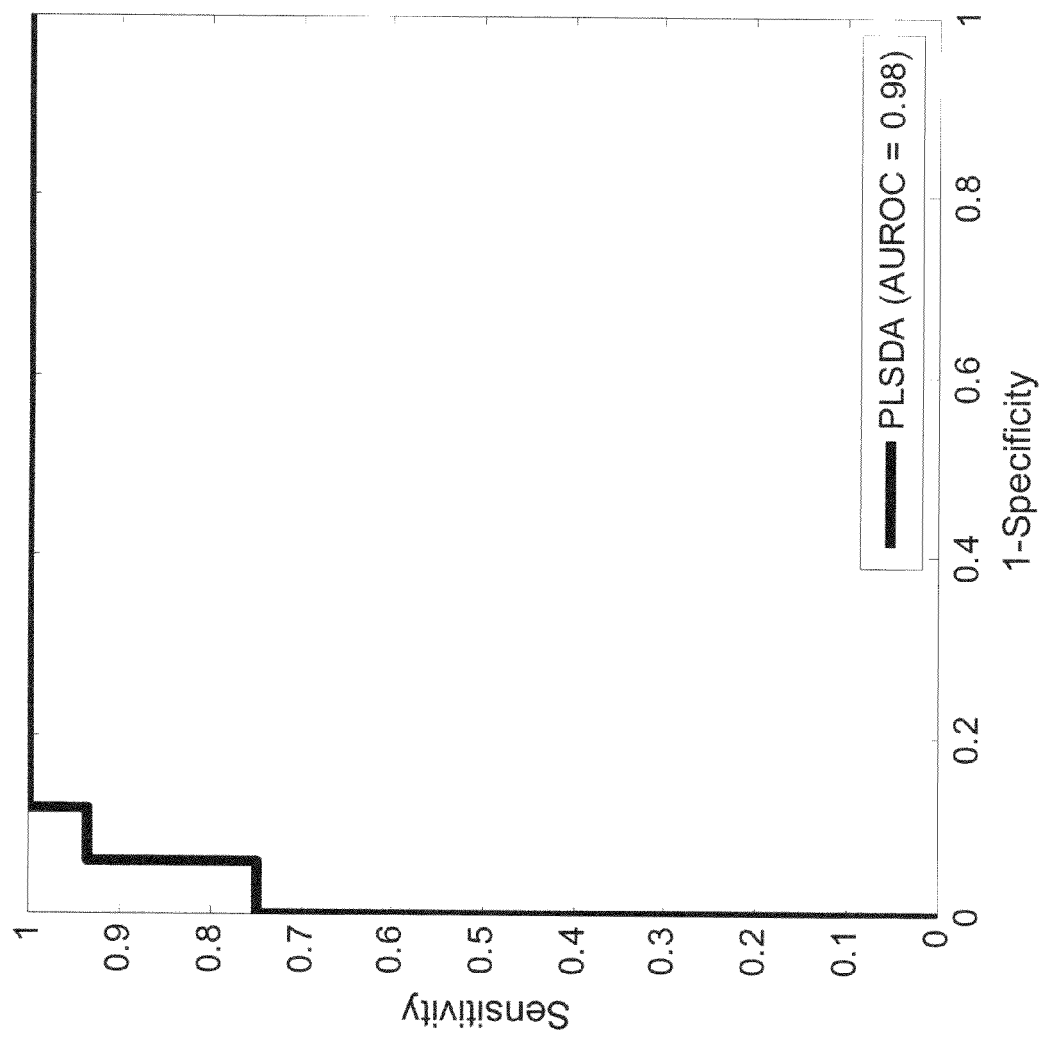
FIG. 11 is illustrative of a receiver operating characteristic (ROC) curve of an exemplary data set of the present disclosure.

In another example, illustrated by FIGS. 9A-13C, a two-class PLSDA model may be used to detect tumors in both dissected and intact organ samples. FIG. 9A is a brightfield image of a dissected kidney sample comprising a tumor and FIG. 9B is a brightfield image of an intact kidney sample comprising a tumor. Average kidney absorbance spectra representative of tumor and non-tumor (NRP and fat) are illustrated in FIG. 10. The average spectra in FIG. 10 are representative of one or more views from seventeen total patients (thirty-three tumor views and thirty-three NRP and fat views). A ROC curve illustrative of the sensitivity and specificity of the model is illustrated in FIG. 11.

FIG. 12A is illustrative of a score image of a dissected kidney sample comprising a tumor. FIG. 12B is illustrative of a score image of an intact kidney sample. As can be seen from the figures, tumors can be detected in both intact and dissected samples. FIG. 12C is illustrative of a digitally stained tumor image, where tumor is colored green and non-tumor is colored blue.

FIGS. 13A-13E are illustrative of the detection capabilities of another embodiment of the present disclosure. Here, a kidney sample is analyzed using a two-class PLSDA model to distinguish between areas of the sample comprising tumor and areas of the sample comprising NRP and fat. FIG. 13A is a brightfield image of the sample. Annotated truth is illustrated in FIG. 13B. Score images generated using a two-class model are illustrated in FIGS. 13C (fat and NRP) and 13D. FIG. 13E is illustrative of a digitally stained image, wherein tumor is green and non-tumor (fat and NRP) are blue. As can be seen comparing FIG. 13B and FIG. 13E, the system and method of the present disclosure hold potential for accurately detecting tumors in organ samples.

Traditional PLSDA provides for the use of a two-class model. However, the present disclosure contemplates that a "three-class" model may be constructed by iteratively applying PLSDA for three characteristics of a biological sample (such as three anatomical features or tumor v. two anatomical features).

As with a two-class PLSDA model, pre-processing such as spectral truncation and vector normalization may be applied. A model may be built for each class (characteristic of the sample). The present disclosure contemplates at least two ways to build the models. First, an approach similar to traditional two-class PLSDA model building may be used. Here, the model uses one characteristic as one class (the target) and combines the other characteristics into the second class.

For example, when analyzing three features of a kidney under analysis such as tumor, fat, and normal renal parenchyma (NRP), the models may be constructed as follows:

| Model | Target | Non-Target |
|---|---|---|
| 1 | Tumor | Fat and NRP |
| 2 | Fat | Tumor and NRP |
| 3 | NRP | Tumor and Fat |

Score images may be generated for target and non-target classes for each model. In one embodiment, a mask may be applied to each score image to mask out the background. An RGB image may be generated representative of the biological sample. In one embodiment, the target score image from each model may be used for each channel of the RGB image (for example, red, green, and blue channels). In another embodiment, a threshold of one model may be applied to it score image to create a mask for that class. The score image may be multiplied by the detection mask and used as one channel of the RGB image. The other two score images may be multiplied by the compliment of the mask and these images may be used for the other two channels of the RGB image.

In another embodiment, the present disclosure provides for a tiered approach to generating a PLSDA model. Here, For example, when analyzing three characteristics of a kidney under analysis such as tumor, fat, and NRP, the models may be constructed as follows:

| Model | Target | Non-Target |
|---|---|---|
| 1 | Fat | Tumor and NRP |
| 2 | Tumor | NRP |

Figure 14:
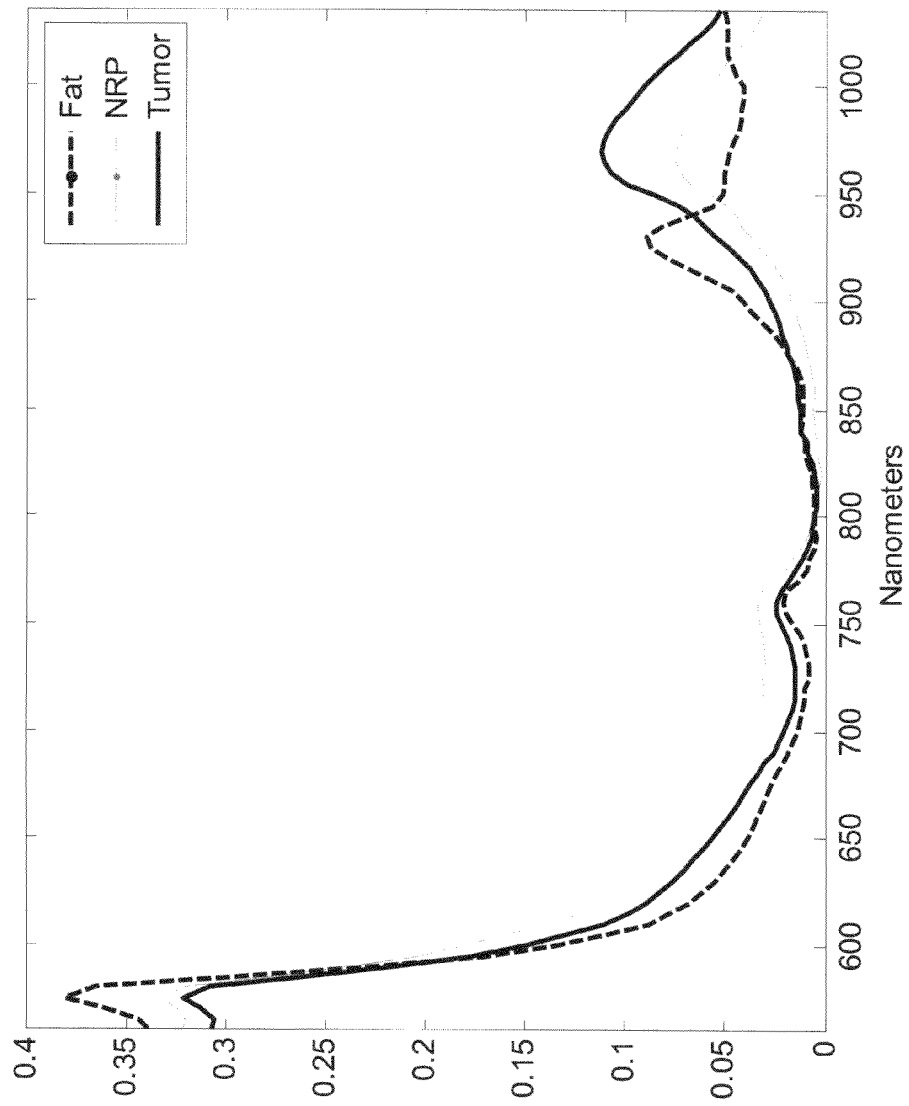
FIG. 14 is illustrative of average kidney absorbance spectra that may be extracted from hyperspectral image data according to the system and method of the present disclosure.
Figures 15A, 15B, 15C:
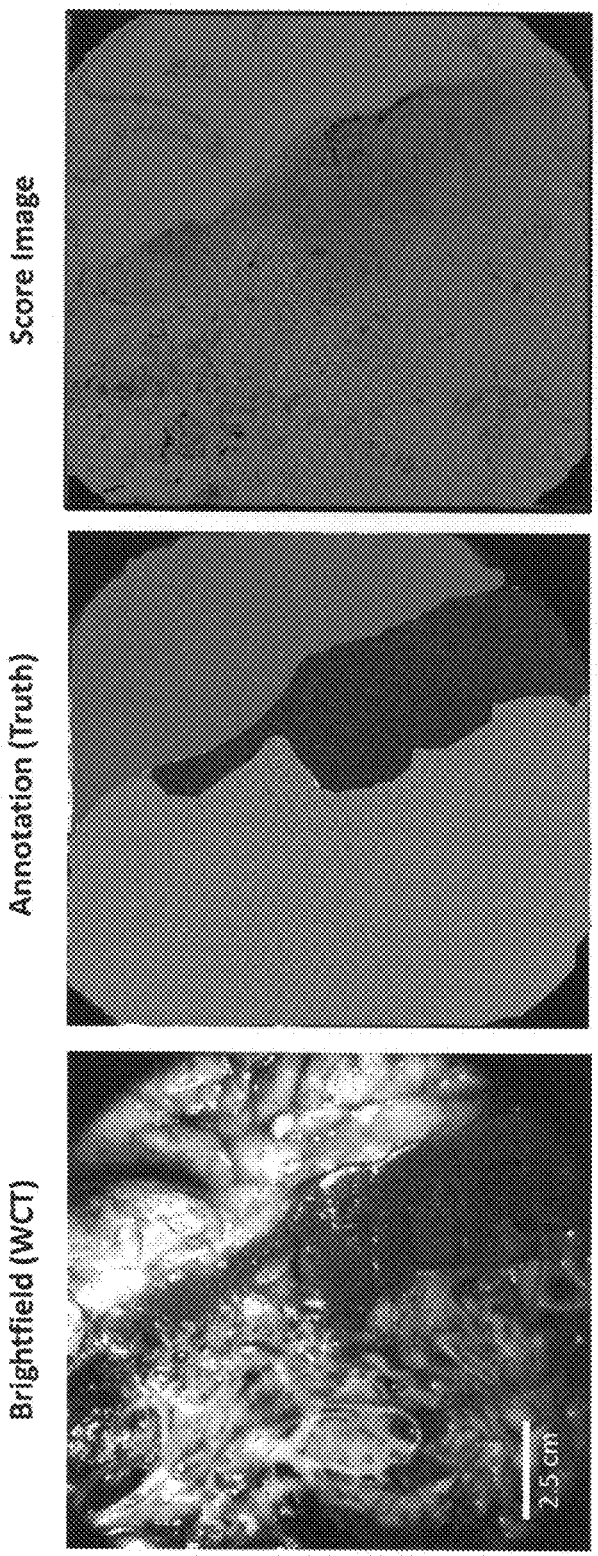
FIGS. 15A-15C are illustrative of the detection capabilities of the present disclosure for distinguishing between tumor, fat, and NRP.

Examples of a three-class approach are illustrated in FIGS. 14-15C. Average kidney absorbance spectra corresponding to fat, NRP, and tumor are illustrated in FIG. 14. FIG. 15A is representative of a brightfield image of a kidney sample and FIG. 15B is representative of annotated truth. A score image, FIG. 15C, is a digitally stained image and illustrates the capability of the system and method of the present disclosure for distinguishing between three characteristics of the sample (tumor is colored green, fat is colored red, and NRP is colored blue).

While the examples described herein are illustrative of the application of PLSDA, the present disclosure is not limited to only this chemometric technique and others known in the art may be applied. For example, as illustrated in FIGS. 16A-16C, PCA may be used. FIG. 16A is a brightfield image of a kidney sample. A score image generated using PCA analysis is illustrated in FIG. 16B. Here, a ureter is distinguished from the rest of the kidney sample. Average absorbance spectra representative of ureter and fat are illustrated in FIG. 16C.

Figure 17:
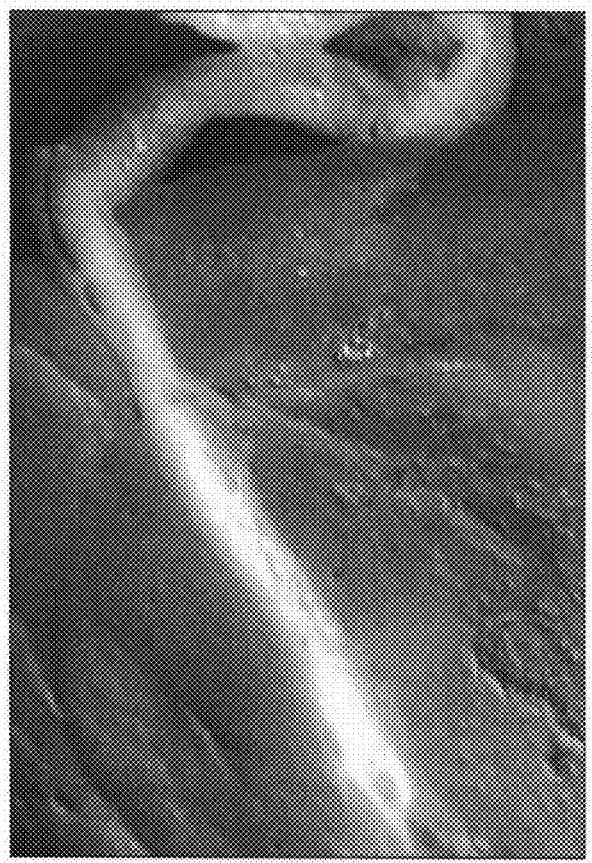
FIG. 17 is illustrative of the detection capabilities of the present disclosure for distinguishing between fat and ureter of a kidney sample by applying a ratiometric technique.

FIG. 17 is illustrative of the detection capabilities of the present disclosure for distinguishing between fat and ureter of a kidney sample by applying a ratiometric technique (wavelength division). Here, images were generated at wavelengths corresponding to 915 nm and 970 nm. However, the present disclosure is not limited to these wavelengths and others may be used for analyzing the images.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the embodiments of the disclosure, it is noted that other variations and modification will be apparent to those skilled in the art, and may be made without departing from the spirit or scope of the disclosure.

What is claimed is:

1. A method of analyzing a biological organ, the method comprising:
    illuminating the biological organ to generate a first plurality of interacted photons;
    collecting the first plurality of interacted photons to generate a first optical signal;
    separating the first optical signal into a plurality of orthogonally polarized optical components;
    filtering the plurality of optical components into a plurality of passband wavelengths to generate a plurality of filtered photons;
    detecting the plurality of filtered photons to generate at least one hyperspectral image; and
    analyzing the at least one hyperspectral image by extracting a spectrum from a location in the at least one hyperspectral image, wherein the location corresponds to an area of interest of the biological organ, and analyzing the extracted spectrum to identify a characteristic of the biological organ.

2. The method of claim 1, wherein the biological organ comprises one or more of a kidney, a ureter, a prostate, a penis, a testicle, a bladder, a heart, a brain, a liver, a lung, a colon, an intestine, a pancreas, a thyroid, an adrenal gland, a spleen, a stomach, a uterus, and an ovary.

3. The method of claim 1, further comprising generating a bright-field image representative of the biological organ.

4. The method of claim 3, further comprising analyzing the bright-field image to identify one or more of a morphological feature of the biological-organ and an anatomical feature of the biological organ.

5. The method of claim 1, wherein analyzing the extracted spectrum further comprises comparing the extracted spectrum to a reference spectrum associated with a known characteristic.

6. The method of claim 5, wherein the comparing comprises applying an algorithmic technique.

7. The method of claim 6, wherein the algorithmic technique comprises support vector machines.

8. The method of claim 6, wherein the algorithmic technique comprises a chemometric technique.

9. The method of claim 8, wherein the chemometric technique comprises one or more of a multivariate curve resolution analysis, a principle component analysis (PCA), a partial least squares discriminant analysis (PLSDA), a k means clustering analysis, a band t. entropy method analysis, an adaptive subspace detector analysis, a cosine correlation analysis, an Euclidian distance analysis, a partial least squares regression analysis, a spectral mixture resolution analysis, a spectral angle mapper metric analysis, a spectral information divergence metric analysis, a Mahalanobis distance metric analysis, and a spectral unmixing analysis.

10. The method of claim 8, wherein the chemometric technique is applied to spectra corresponding to each pixel of the at least one hyperspectral image to generate at least one score image.

11. The method of claim 10, wherein the score image comprises one or more of a target image and a non-target image.

12. The method of claim 11, further comprising applying a threshold to the target image to generate a class image of the biological organ.

13. The method of claim 11, further comprising generating an RGB image of the biological organ, wherein at least one channel of the RGB image corresponds to the target image.

14. The method of claim 11, further comprising generating an RGB image of the biological organ, wherein at least one channel of the RGB image corresponds to a non-target image.

15. The method of claim 1, wherein at least two hyperspectral images are generated and the analyzing comprises applying at least one ratiometric technique.

16. The method of claim 1, wherein the characteristic comprises an anatomical feature of the biological organ.

17. The method of claim 1, wherein the characteristic comprises one or more of a tumor and a non-tumor.

18. The method of claim 17, wherein the tumor comprises one or more of a cancerous tumor and a non-cancerous tumor.

19. The method of claim 1, wherein the characteristic comprises a tumor margin.

20. The method of claim 1, wherein the hyperspectral image comprises a VIS-NIR hyperspectral image.

21. The method of claim 1, wherein the plurality of orthogonally polarized optical components comprises a first optical component and a second optical component, and the filtering comprises transmitting the first optical component to a first optical filter to generate a first portion of the plurality of filtered photons and transmitting the second optical component to a second optical filter to generate a second portion of the plurality of filtered photons.

22. The method of claim 21, wherein detecting the plurality of filtered photons comprises detecting the first portion of the plurality of filtered photons with a first detector and detecting the second portion of the plurality of filtered photons with a second detector.

23. The method of claim 21, wherein the first portion of the plurality of filtered photons and the second portion of the plurality of filtered photons are detected substantially simultaneously.

24. The method of claim 21, wherein the first portion of the plurality of filtered photons and the second portion of the plurality of filtered photons are detected sequentially.

25. The method of claim 21, wherein the hyperspectral image generated from the first portion of the plurality of filtered photons and the hyperspectral image generated from the second portion of the plurality of filtered photons are overlaid.

26. The method of claim 21, wherein the hyperspectral image generated from the first portion of the plurality of filtered photons and the hyperspectral image generated from the second portion of the plurality of filtered photons are not overlaid.

27. The method of claim 1, wherein filtering comprises passing the plurality of optical components through a tunable filter further comprising one or more of a fixed filter and a tunable filter.

28. A system for analyzing a biological organ, the system comprising:
an illumination source configured to illuminate the biological organ and generate a first plurality of interacted photons;
a collection optic configured to collect the first plurality of interacted photons and generate a first optical signal;
a beam splitter configured to separate the first optical signal into a plurality of optical components;
a plurality of filters, wherein each filter is configured to filter one of the plurality of optical components into a passband wavelength to generate a plurality of filtered components;
one or more detectors configured to detect the plurality of filtered components and generate at least one hyperspectral image; and
a processor configured to analyze the at least one hyperspectral image by extracting a spectrum from a location in the at least one hyperspectral image, wherein the location corresponds to an area of interest of the biological organ, and analyzing the extracted spectrum to identify a characteristic of the biological organ.

29. The system of claim 28, wherein the plurality of optical components comprises a first optical component having a first polarization alignment and a second optical component having a second polarization alignment.

30. The system of claim 29, wherein the plurality of filters comprises a first filter configured to receive the first optical component and transmit at least a portion of the first optical component having a first wavelength and a second filter configured to receive the second optical component and transmit at least a portion of the second optical component having a second wavelength.

31. The system of claim 30, wherein the one or more detectors comprises a detector configured to detect the first optical component and the second optical component.

32. The system of claim 30, wherein the one or more detectors comprises a first detector configured to detect the first optical component and a second detector configured to detect the second optical component.

33. The system of claim 28, wherein the illumination source comprises one or more of a metal halide arc lamp and a quartz tungsten halogen lamp.

34. The system of claim 28, further comprising a tissue bin configured to hold the biological organ.

35. The system of claim 28, wherein the collection optic comprises a zoom lens.

36. The system of claim 28, further comprising a controller configured to tune one or more of the plurality of filters to at least one wavelength band.

37. The system of claim 36, wherein the controller is further configured to tune one or more of the plurality of filters to a wavelength band in the range of about 400 nm to about 1100 nm.

38. The system of claim 28, wherein one or more of the plurality of filters comprises one or more of a fixed filter and a tunable filter.

39. The system of claim 38, wherein the tunable filter further comprises one or more of a Fabry Perot angle tunable filter, an acousto-optic tunable filter, a liquid crystal tunable filter, a Lyot filter, an Evans split element liquid crystal tunable filter, a Solc liquid crystal tunable filter, a fixed wavelength Fabry Perot tunable filter, an air-tuned Fabry Perot tunable filter, a mechanically-tuned Fabry Perot tunable filter, and a liquid crystal Fabry Perot tunable filter.

40. The system of claim 28, wherein the one or more detectors comprise an InGaAs detector, a photodiode array detector, a CMOS detector, an InSb detector, a CCD detector, an ICCD detector, and an MCT detector.

41. The system of claim 28, wherein the processor further comprises at least one reference data set wherein each reference data set is associated with a known characteristic.

42. The system of claim 28, wherein the processor is further configured to compare the extracted spectrum to the at least one reference data set.

43. The system of claim 28, wherein the one or more detectors are further configured to generate a bright field image of the biological organ.

44. A system comprising:
a processor; and
a non-transitory data storage medium containing program code, which, when executed by a processor, causes the processor to:
  illuminate a biological organ to generate a plurality of interacted photons;
  collect the plurality of interacted photons to generate a first optical signal;
  transmit the first optical signal through a beam splitter to separate the first optical signal into a plurality of optical components;
  pass the plurality of optical components through a plurality of tunable filters, wherein each filter is configured to filter one of the plurality of optical components into a passband wavelength to generate a plurality of filtered components;
  detect the plurality of filtered components with one or more detectors to generate at least one hyperspectral image;
  generate a bright field image representative of the biological organ;
  align the bright field image with the at least one hyperspectral image;
  extract a spectrum from a location of the at least one hyperspectral image, wherein each location corresponds to an area of interest of the biological organ;
  analyze the extracted spectrum to identify a characteristic of the biological organ.

45. The system of claim 44, wherein the storage medium further contains one or more programming instructions that, when executed, cause the processor to:
  transmit a first optical component of the plurality of optical components to a first tunable filter and a second optical component of the plurality of optical components to a second optical filter.

* * * * *